United States Patent
Park et al.

(10) Patent No.: US 11,647,961 B2
(45) Date of Patent: May 16, 2023

(54) ELECTRONIC DEVICE FOR MEASURING INFORMATION REGARDING HUMAN BODY AND OPERATING METHOD THEREOF

(71) Applicant: Samsung Electronics Co., Ltd., Suwon-si (KR)

(72) Inventors: Sang-Bae Park, Suwon-si (KR);
Do-Yoon Kim, Seongnam-si (KR);
Young-Hyun Kim, Suwon-si (KR);
Byung-Hun Choi, Suwon-si (KR);
Jae-Eun Kang, Suwon-si (KR);
Chang-Hyun Kim, Seoul (KR);
Kang-Jin Yoon, Seoul (KR);
Jeong-Eun Lee, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 554 days.

(21) Appl. No.: 16/823,878

(22) Filed: Mar. 19, 2020

(65) Prior Publication Data

US 2020/0214638 A1    Jul. 9, 2020

Related U.S. Application Data

(63) Continuation of application No. 15/176,823, filed on Jun. 8, 2016, now Pat. No. 10,595,783.

(30) Foreign Application Priority Data

Jun. 19, 2015    (KR) .................. 10-2015-0087658

(51) Int. Cl.
*A61B 5/00*    (2006.01)
*G06F 3/041*    (2006.01)
(Continued)

(52) U.S. Cl.
CPC .......... *A61B 5/6898* (2013.01); *A61B 5/0022* (2013.01); *A61B 5/4869* (2013.01);
(Continued)

(58) Field of Classification Search
CPC ... A61B 5/6898; A61B 5/0022; A61B 5/4869; G16H 40/67; G06F 3/0416; G06F 1/163
See application file for complete search history.

(56) References Cited

U.S. PATENT DOCUMENTS 6,400,983 B1 * 6/2002 Cha .................... A61B 5/0537
600/547
2006/0122533 A1 6/2006 Park et al.
(Continued)

FOREIGN PATENT DOCUMENTS

JP    2001-145607 A    5/2001
KR   10-2001-0017248 A    3/2001
(Continued)

OTHER PUBLICATIONS

Korean Office Action dated Jan. 13, 2022, issued in Korean Application No. 10-2015-0087658.

*Primary Examiner* — Daniel L Cerioni
(74) *Attorney, Agent, or Firm* — Jefferson IP Law, LLP

(57) ABSTRACT

An electronic device and method for measuring user body information are provided. The method for measuring user body information includes detecting a contact of a user's body portion on at least two spots of a touch screen of the electronic device, upon detecting the contact of the user's body portion on the at least two spots of the touch screen, applying power to a first coil in the electronic device, and measuring the user body information using at least one of a voltage and a second current measured after a first current is induced across the user's body by a first magnetic field generated from the first coil as the power is applied.

20 Claims, 31 Drawing Sheets

(51) Int. Cl.
*G16H 40/67* (2018.01)
*A61B 5/024* (2006.01)
*A61B 5/01* (2006.01)
*A61B 5/055* (2006.01)
*A61B 5/0537* (2021.01)
*A61B 5/145* (2006.01)
*G06F 3/0488* (2022.01)
*G06F 1/16* (2006.01)

(52) U.S. Cl.
CPC ........... *G06F 3/0416* (2013.01); *G16H 40/67* (2018.01); *A61B 5/01* (2013.01); *A61B 5/024* (2013.01); *A61B 5/055* (2013.01); *A61B 5/0537* (2013.01); *A61B 5/14532* (2013.01); *A61B 5/4872* (2013.01); *A61B 5/4875* (2013.01); *G06F 1/163* (2013.01); *G06F 3/0488* (2013.01)

(56) References Cited

U.S. PATENT DOCUMENTS

| | | |
|---|---|---|
| 2006/0283748 A1 | 12/2006 | Daio et al. |
| 2010/0079399 A1 | 4/2010 | Ma |
| 2013/0141116 A1 | 6/2013 | Feldkamp et al. |
| 2015/0207913 A1 | 7/2015 | Nakano et al. |
| 2016/0210616 A1* | 7/2016 | Lee ..................... H04B 5/0031 |

FOREIGN PATENT DOCUMENTS

| | | |
|---|---|---|
| KR | 10-2005-0071841 A | 7/2005 |
| KR | 10-2006-0040497 A | 5/2006 |
| KR | 10-2008-0010688 A | 1/2008 |
| KR | 10-2014-0023096 A | 2/2014 |
| KR | 10-2014-0030711 A | 3/2014 |
| KR | 10-2015-0003553 A | 1/2015 |

* cited by examiner

ELECTRONIC DEVICE FOR MEASURING INFORMATION REGARDING HUMAN BODY AND OPERATING METHOD THEREOF

CROSS-REFERENCE TO RELATED APPLICATION(S)

This application is a continuation application of prior application Ser. No. 15/176,823, filed on Jun. 8, 2016, which claims the benefit under 35 U.S.C. § 119(a) of a Korean patent application filed on Jun. 19, 2015 in the Korean Intellectual Property Office and assigned Serial No. 10-2015-0087658, the entire disclosure of each of which is hereby incorporated by reference.

TECHNICAL FIELD

The present disclosure relates to electronic devices for measuring information regarding a user's body and methods for the same. More particularly, the present disclosure relates to electronic devices for measuring information regarding a user's body using electromagnetic induction methods and methods for the same.

BACKGROUND

As the use of smartphones or tablet personal computers (PCs) spreads, more and more people use an application installed on such gadget to monitor their health and body conditions during workouts. A user of such application may improve his health by managing his weight, diet, and other health issues with the application. Such application may offer the user body information that assists the user in staying healthy, and the user may select a healthy workout or diet by checking his body information.

Typical body information checkable by the user includes, e.g., body fat, body composition, and body water. Such body information may help to prevent various adult diseases. The amount of fat in a human body may be defined as the body fat. An increase in the body fat may sharply increase the occurrence of stroke, heart attack, or other vascular diseases and other adult diseases. Accordingly, the body fat has various applications as a health index.

The body information including body fat, body composition, or body water may be influenced by lifestyle, such as diet or exercise. Thus, a need exists for steady measurement and management of such body information as well as weight by an electronic device such as a smartphone, a tablet PC, or a wearable device.

A device for measuring body information such as body fat according to the related art applies current to the user's body using electrodes. However, the electrodes are disposed outside the device, thus harming the design and appearance. The electrodes need to be positioned outside the device and are difficult to embed in a portable terminal. The need of the user to directly contact the electrodes increases the risk of electric shocks and germ contamination.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method and device for measuring body information for addressing the foregoing or other issues.

In accordance with an aspect of the present disclosure, a method for measuring user body information is provided. The method includes detecting a contact of a user's body portion on at least two spots of a touch screen of the electronic device, upon detecting the contact of the user's body portion on the at least two spots of the touch screen, applying power to a first coil in the electronic device, and measuring the user body information using at least one of a voltage and a second current measured after a first current is induced across the user's body by a first magnetic field generated from the first coil as the power is applied.

In accordance with another aspect of the present disclosure, an electronic device for measuring user body information is provided. The electronic device includes a touch screen, a first coil disposed under the touch screen, and a processor configured to detect a contact of a user's body portion on at least two spots of the touch screen, upon detecting the contact of the user's body portion on at least two spots of the touch screen, apply power to the first coil in the electronic device, and measure the user body information using at least one of a voltage and a second current measured after a first current is induced across the user's body by a first magnetic field generated from the first coil as the power is applied.

In accordance with another aspect of the present disclosure, a method for measuring user body information by an electronic device is provided. The method includes detecting a contact of a user's body portion on a touch screen of the electronic device, upon detecting the contact of the user's body portion on the touch screen, applying a first current to the user's body through an electrode included in the electronic device, measuring a second current induced across a first coil in the electronic device by a first magnetic field generated by the first current, and measuring the user body information using the measured second current.

In accordance with another aspect of the present disclosure, an electronic device for measuring user body information is provided. The electronic device includes a touch screen, an electrode applying a current, a first coil disposed under the touch screen, and a processor configured to detect a contact of a user's body portion on the touch screen, upon detecting the contact of the user's body portion on the touch screen, apply a first current to the user's body through the electrode, measure a second current induced across the first coil by a first magnetic field generated by the first current, and measure the user body information using the measured second current.

In accordance with another aspect of the present disclosure, a method for operating an electronic device is provided. The method includes measuring at least one of a current and voltage induced across a coil embedded in the electronic device by a magnetic field generated from outside the electronic device and selecting one of measuring user body information and charging the electronic device based on the at least one of the measured current and voltage.

In accordance with another aspect of the present disclosure, an electronic device is provided. The electronic device includes a coil and a processor configured to measure at least one of a current and voltage induced across the coil embedded in the electronic device by a magnetic field generated from outside the electronic device and select one of measuring user body information and charging the electronic device based on the at least one of the measured current and voltage.

According to embodiments of the present disclosure, the electronic device may measure user body information using a coil according to the electromagnetic induction law. The coil is embedded in the electronic device, avoiding a design deterioration of the electronic device. Further, since the user's body does not directly contact the electrodes, the user may be prevented from electric shocks or germ contamination in measuring his body information. Further, the coils may be used to wirelessly the electronic device without adding a separate hardware component.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
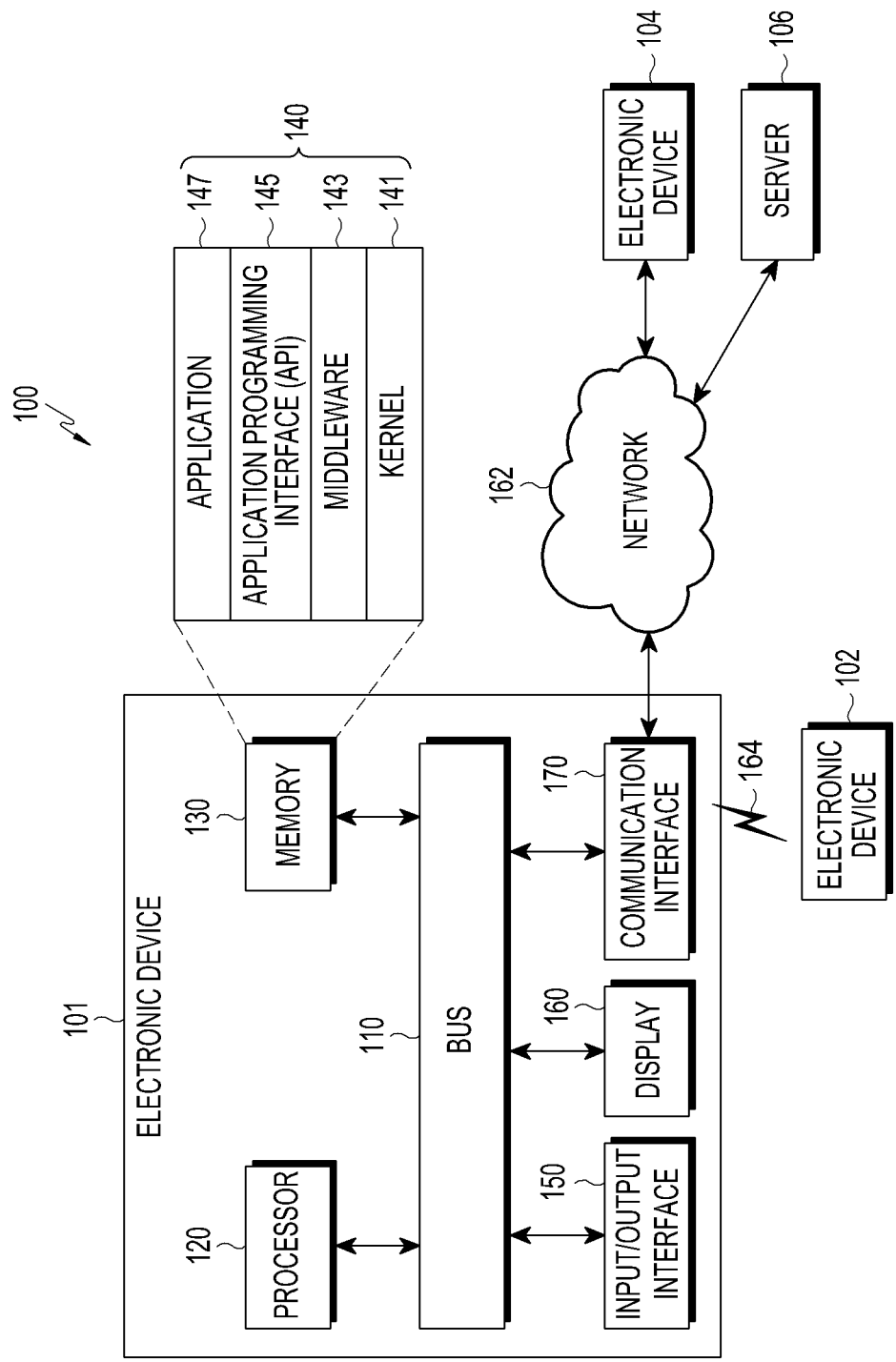
FIG. 1 illustrates a network environment including an electronic device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary.

Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used herein, the terms "have," "may have," "include," or "may include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and/or order and are used to distinguish a component from another without limiting the components. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts. For example, the term "processor configured (or set) to perform A, B, and C" may mean a generic-purpose processor (e.g., a central processing unit (CPU) or application processor (AP)) that may perform the operations by executing one or more software programs stored in a memory device or a dedicated processor (e.g., an embedded processor) for performing the operations.

The terms as used herein are provided merely to describe some embodiments thereof, but not to limit the scope of other embodiments of the present disclosure. It is to be understood that the singular forms "a," "an," and "the" include plural references unless the context clearly dictates otherwise. The terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a personal digital assistant (PDA), a portable multimedia player (PMP), an Moving Picture Experts Group phase 1 or phase 2 (MPEG-1 or MPEG-2) audio layer 3 (MP3) player, a mobile medical device, a camera, or a wearable device. According to an embodiment of the present disclosure, the wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device (e.g., an implantable circuit).

According to an embodiment of the present disclosure, the electronic device may be a home appliance. For example, the smart home appliance may include at least one of a television (TV), a digital versatile disc (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame.

According to an embodiment of the present disclosure, examples of the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or Internet of things (IoT) devices (e.g., a bulb, various sensors, an electric or gas meter, a sprinkler, a fire alarm, a thermostat, a street light, a toaster, fitness equipment, a hot water tank, a heater, or a boiler).

According to various embodiments of the disclosure, examples of the electronic device may include at least one of part of furniture or building/structure, an electronic board, an electronic signature receiving device, a projector, or various measurement devices (e.g., devices for measuring water, electricity, gas, or electromagnetic waves). According to an embodiment of the present disclosure, the electronic device may be one or a combination of the above-listed devices. According to an embodiment of the present disclosure, the electronic device may be a flexible electronic device. The electronic device disclosed herein is not limited to the above-listed devices, and may include new electronic devices depending on the development of technology.

Hereinafter, electronic devices are described with reference to the accompanying drawings, according to various embodiments of the present disclosure. As used herein, the term "user" may denote a human or another device (e.g., an artificial intelligent electronic device) using the electronic device.

FIG. 1 illustrates a network environment including an electronic device according to an embodiment of the present disclosure.

Referring to FIG. 1, according to an embodiment of the present disclosure, an electronic device 101 is included in a network environment 100. The electronic device 101 may include a bus 110, a processor 120, a memory 130, an input/output interface 150, a display 160, and a communication interface 170. In some embodiments of the present disclosure, the electronic device 101 may exclude at least one of the components or may add another component.

The bus 110 may include a circuit for connecting the components 110 to 170 with one another and transferring communications (e.g., control messages and/or data) between the components.

The processing module 120 may include one or more of a CPU, an AP, or a communication processor (CP). The processor 120 may perform control on at least one of the other components of the electronic device 101, and/or perform an operation or data processing relating to communication.

The memory 130 may include a volatile and/or non-volatile memory. For example, the memory 130 may store commands or data related to at least one other component of the electronic device 101. According to an embodiment of the present disclosure, the memory 130 may store software and/or a program 140. The program 140 may include, e.g., a kernel 141, middleware 143, an application programming interface (API) 145, and/or an application program (or "application") 147. At least a portion of the kernel 141, middleware 143, or API 145 may be denoted an operating system (OS).

For example, the kernel 141 may control or manage system resources (e.g., the bus 110, processor 120, or a memory 130) used to perform operations or functions implemented in other programs (e.g., the middleware 143, API 145, or application program 147). The kernel 141 may provide an interface that allows the middleware 143, the API 145, or the application 147 to access the individual components of the electronic device 101 to control or manage the system resources.

The middleware 143 may function as a relay to allow the API 145 or the application 147 to communicate data with the kernel 141, for example.

Further, the middleware 143 may process one or more task requests received from the application program 147 in order of priority. For example, the middleware 143 may assign at least one of application programs 147 with priority of using system resources (e.g., the bus 110, processor 120, or memory 130) of at least one electronic device 101. For example, the middleware 143 may perform scheduling or load balancing on the one or more task requests by processing the one or more task requests according to the priority assigned to the at least one application program 147.

The API 145 is an interface allowing the application 147 to control functions provided from the kernel 141 or the middleware 143. For example, the API 145 may include at least one interface or function (e.g., a command) for filing control, window control, image processing or text control.

The input/output interface 150 may serve as an interface that may, e.g., transfer commands or data input from a user or other external devices to other component(s) of the electronic device 101. Further, the input/output interface 150 may output commands or data received from other component(s) of the electronic device 101 to the user or the other external device.

The display 160 may include, e.g., a liquid crystal display (LCD), a light emitting diode (LED) display, an organic LED (OLED) display, or a microelectromechanical systems (MEMS) display, or an electronic paper display. The display 160 may display, e.g., various contents (e.g., text, images, videos, icons, or symbols) to the user. The display 160 may include a touch screen and may receive, e.g., a touch, gesture, proximity or hovering input using an electronic pen or a body portion of the user.

The communication interface 170 may set up communication between the electronic device 101 and an external electronic device (e.g., a first electronic device 102, a second electronic device 104, or a server 106). For example, the communication interface 170 may be connected with a network 162 through wireless or wired communication to communicate with the external electronic device.

The wireless communication may be a cellular communication protocol and may use at least one of, e.g., long-term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM). Further, the wireless communication may include, e.g., short-range communication 164. The short-range communication 164 may include at least one of Wi-Fi, Bluetooth, near-field communication (NFC), or global navigation satellite system (GNSS). The GNSS may include at least one of, e.g., global positioning system (GPS), global navigation satellite system (Glonass), Beidou navigation satellite system (hereinafter, "Beidou") or Galileo, or the European global satellite-based navigation system. Hereinafter, the terms "GPS" and the "GNSS" may be interchangeably used herein. The wired connection may include at least one of, e.g., universal serial bus (USB), high definition multimedia interface (HDMI), recommended standard (RS)-232, or plain old telephone service (POTS). The network 162 may include at least one of telecommunication networks, e.g., a computer network (e.g., local area network (LAN) or wireless area network (WAN)), Internet, or a telephone network.

The first and second external electronic devices 102 and 104 each may be a device of the same or a different type from the electronic device 101. According to an embodiment of the present disclosure, the server 106 may include a group of one or more servers. According to an embodiment of the present disclosure, all or some of operations executed on the electronic device 101 may be executed on another or multiple other electronic devices (e.g., the electronic devices 102 and 104 or server 106). According to an embodiment of the present disclosure, when the electronic device 101 should perform some function or service automatically or at a request, the electronic device 101, instead of executing the function or service on its own or additionally, may request another device (e.g., electronic devices 102 and 104 or server 106) to perform at least some functions associated therewith. The other electronic device (e.g., electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

The processor 120 may process at least part of information obtained from other elements (e.g., at least one of the memory 130, the input/output interface 150, or the communication interface 170) and may use the same in various manners. For example, the processor 120 may control at least some functions of the electronic device 101 so that the electronic device 101 may interwork with another electronic device (e.g., the electronic device 102 or 104 or the server 106). The processor 120 may be integrated with the communication interface 170.

According to an embodiment of the present disclosure, at least one configuration of the processor 120 may be included in the server 106 and may be supported for at least one operation implemented on the processor 120 from the server 106.

According to an embodiment of the present disclosure, the memory 130 may include instructions enabling the processor 120 to operate. For example, the memory 130 may include instructions enabling the processor 120 to control other components of the electronic device 101 and to interwork with other electronic devices 102 and 104 or the server 106.

The processor 120 may control other components of the electronic device 101 and interwork with the other electronic devices 102 and 104 or the server 106 based on the instructions stored in the memory 130.

Hereinafter, operations of the electronic device 101 are described based on each component of the electronic device 101. The instructions enabling the components to operate may be included in the memory 130.

According to an embodiment of the present disclosure, the processor 120 may detect contacts of a user's body portion to at least two spots on the touch screen of the electronic device 101.

For example, the processor 120 may identify at least one of the contact area, contact position, and contact time for the user's body portion. Further, the processor 120 may detect the contact of the user's body portion based on the identified result.

When the user simply touches his body portion to the touch screen and immediately takes it off the touch screen, the information regarding the user's body (simply, referred herein as to "user body information" or "body information") might not be exactly measured.

For example, current might not be properly induced across the user's body, or at least one of current and voltage induced through a coil included in the electronic device 101 by a magnetic field generated by current induced across the user's body might not correctly measured.

Accordingly, the processor 120 may detect the contact of the user's body by identifying at least one of the contact area, contact position, and contact time.

According to an embodiment of the present disclosure, at least two spots of the touch screen may be previously set and displayed on the touch screen. Accordingly, the user may intuitively notice the contact spots of the body portion for measuring body information.

According to an embodiment of the present disclosure, when detecting the contacts of the user's body portion on at least two spots of the touch screen, the processor 120 may apply power to a first coil in the electronic device 101. The power may be applied corresponding to the user's input.

When the electronic device 101 is away from the user's body, as the power is applied, it may be difficult to induce a first current across the user's body by a first magnetic field generated by the first coil included in the electronic device 101.

Further, generating the first magnetic field regardless of the user's intention may cause unnecessary power consumption. Thus, the processor 120 may apply power to the first coil by detecting a contact of the user's body portion.

When power is applied to the first coil in the electronic device 101, the first magnetic field may be generated by an electromagnetic induction law. The first magnetic field may be generated in a direction from the inside of the electronic device 101 to the touch screen.

For example, power sources for supplying the power to the first coil may include a direct current (DC) power source, e.g., a battery, steadily supplying the same power and an alternating current (AC) power source supplying alternating power.

The type of the power sources may include a voltage source and a current source. The voltage source does not change voltage by the magnitude of current, and the current source does not change current by the magnitude of voltage. There may be a constant power source and a variable power source; the former provides constant voltage or frequency while the latter provides variable voltage or frequency.

The characteristics of the AC may be represented with frequency, amplitude, and waveform depending on the magnitude, variation rate, and stability of voltage or current. For example, the power applied to the first coil may be a current or voltage. The voltage of the voltage source may be set to be the same as the voltage used in the electronic device including the first coil. The current source may be an AC current source. The alternating period of current may be previously set so that the first magnetic field may have a predetermined frequency. The predetermined frequency may be set to a frequency that is efficient and appropriate for measuring user body information, such as body composition information, body fat information, body fat-free information, body water information, body muscle information, body protein information, and body mineral information.

For example, in order to measure the user body information, the predetermined frequency may be set to a particular frequency, such as 1 Mhz, 4 Mhz, or 12 Mhz and may be adjusted and set to a proper frequency depending on the type of the user body information.

According to an embodiment of the present disclosure, the first coil may be made in the form of a transparent film and may be inserted in the electronic device 101. For example, the first coil may be processed in the form of a transparent film and put in the electronic device 101 so that the first coil cannot be viewed from outside.

Further, the first coil may be disposed under the touch screen of the electronic device 101. As such, the first coil may be embedded in the electronic device 101 to avoid direct contact with the user's body, leading to a reduced likelihood of electric shock.

For example, the first coil may be, e.g., an air-core coil or core-type coil depending on its components or may be shaped as a spiral, ring, loop, or meander. The air-core coil is a coil wound in the shape of a cylinder with no magnetic iron core therein so that electric current may flow around the axis of the cylinder. The core coil is a coil wound around a bar-shaped, E-shaped, or book-shaped (iron) core. The first coil may have various shapes. When shaped as a spiral, the first coil may be wound around a disc in a similar form to a spider web, and this may be called a spider. Further, the first coil may be a ring coil shaped as a ring, a loop coil shaped as a spiral or helix, or a meander coil with a continuous thunderbolt or swastika pattern. The first coil may be formed of iron, molybdenum, nickel, silicon, aluminum, or a combination thereof.

According to an embodiment of the present disclosure, the first magnetic field generated by the first coil may be used in a blood flow enhancing system.

According to an embodiment of the present disclosure, the processor 120 may measure the user body information using at least one of a second current and voltage measured after the first current is induced across the user's body by the first magnetic field. Further, the processor 120 may output the measured user body information on the touch screen.

According to an embodiment of the present disclosure, when the first magnetic field is generated by the first coil, the first current may be induced across the user's body. For example, the first current may be induced at the whole or part of the user's body depending on where the user's body portion contacts the touch screen.

When the first current is induced across the whole body of the user, the processor 120 may measure information regarding the whole body of the user based on the first current. Likewise, when the first current is induced across a portion of the user's body, the processor 120 may measure information regarding the portion of the user's body based on the first current. Further, the processor 120 may output the measured user body information on the touch screen.

According to an embodiment of the present disclosure, the processor 120 may measure a second current induced across a second coil included in the electronic device 101 by a second magnetic field generated by the first current. The first current may be induced across the user's body by the first magnetic field as per a law of electromagnetic induction (e.g., Faraday's law of induction).

As the first current flows across the user's body, the second magnetic field is generated, inducing the second current across the second coil in the electronic device 101. The processor 120 may measure the second current. The processor 120 may measure the voltage induced across the second coil in a similar manner to that for the second current.

According to an embodiment of the present disclosure, the user body information may include at least one of body composition information, body fat information, body fat-free information, body water information, body muscle information, body protein information, and body mineral information, as for the user's body. However, the user body information is not limited thereto, and it will be apparent to one of ordinary skill in the art that any or everybody information measurable by a current induced across the user's body may be included in the user body information. Hereinafter, the description focuses primarily on body fat information for the purpose of description. However, other types of user body information may also be measured in the same manner except for the process of computing the final information.

According to an embodiment of the present disclosure, like the first coil, the second coil may be made in the form of a transparent film and may be inserted in the electronic device 101.

For example, the second coil may be processed in the form of a transparent film and put in the electronic device 101 so that the first coil cannot be viewed from outside. The second coil may be disposed under the touch screen of the electronic device 101 to avoid direct contact with the user's body.

Accordingly, the first coil and the second coil may operate like contactless electrodes. The second coil may be wound in an opposite direction from a direction that the first coil is wound. Accordingly, magnetic fields generated by application of power to the first and second coils may be oriented in opposite directions.

According to an embodiment of the present disclosure, at least one of the first coil and the second coil may be included in a transparent film. The first coil and the second coil may be wound in different directions. For example, the second coil may be wound in an opposite direction from a direction that the first coil is wound. Accordingly, magnetic fields respectively generated by the first and second coils may be oriented in opposite directions.

Depending on the direction of the generation of the magnetic fields, each of the first coil and the second coil may be operated as one of a source coil externally generating a magnetic field and a reception coil where current or voltage is induced by an external magnetic field. As the first coil and the second coil have more turns, they may have increased sensitivity. The transparent film may include the first coil only or the second coil only or both the first coil and the second coil. The transparent film may include three or more coils.

According to an embodiment of the present disclosure, the processor 120 may measure user body information using the second current. A portion of a human body may be an impedance and electrolyte, and current and voltage may be varied depending on the body fat, protein, minerals, bones, or muscles of the body. Accordingly, the current flowing across the first coil to generate the first magnetic field may be different from the second current induced across the second coil by the second magnetic field generated by the first current, and the user body information may be measured using the second current and the current flowing across the first coil. For example, the processor 120 may calculate the difference between the second current induced across the second coil and the current flowing across the first coil as the power is supplied to measure the user body information. Likewise, the processor 120 may measure the user body information using a voltage induced across the second coil.

According to an embodiment of the present disclosure, the processor 120 may charge the electronic device 101 with a third current induced across the second coil by a third magnetic field generated from outside of the electronic device 101. The processor 120 may wirelessly charge the electronic device 101 with the third current induced across the second coil. As such, the processor 120 may wirelessly charge the electronic device 101 as well as measure the user body information without adding a separate hardware component using the coils in the electronic device 101. Further, the processor 120 may charge the electronic device 101 with a voltage induced across the second coil.

According to an embodiment of the present disclosure, the processor 120 may determine whether to charge the electronic device 101 based on at least one of a user input obtained, running an application related to the charging, the magnitude of the third current, and the magnitude of impedance measured by the third current. For example, the processor 120 may charge the electronic device 101 without measuring the user body information according to the user input. When the charging-related application runs, the electronic device 101 may automatically charge the electronic device 101. In contrast, when an application related to measuring the body information runs, the electronic device 101 may automatically measure the body information.

The processor 120 may identify the load generating the third magnetic field according to the magnitude of the third current. For example, the processor 120 may previously measure the magnitude of current induced by a magnetic field generated by a wireless charger and measure the magnitude of current induced by a magnetic field generated by the human body. The processor 120 may identify the load based on the magnitude of current previously measured, and when the load is identified to be the human body, may measure the user body information. In contrast, the processor 120, when the load is identified to be the wireless charger, may charge the electronic device 101.

Likewise, the processor 120 may identify the load generating the third magnetic field according to the magnitude of impedance measured by the third current. For example, when the magnitude of impedance measured is included in an impedance range of a normal human being, the processor 120 may measure the user body information. In contrast, when the magnitude of impedance measured is included in an impedance range of a normal wireless charger, the processor 120 may charge the electronic device 101.

As such, the processor 120, when the electronic device 101 is determined to be charged, may charge the electronic device 101 using the third current.

The magnitude of current and impedance which are references for identifying the load may be previously set, and the load may be identified through voltage. This is merely for the purpose of description, and it will be apparent to one of ordinary skill in the art that various methods may apply to differentiate the load generating the third magnetic field.

According to an embodiment of the present disclosure, the processor 120 may measure the voltage at one of at least two spots on the touch screen. For example, the processor 120 may measure a voltage sensed at one of at least two spots on the touch screen as the user's body portion contacts the touch screen. The spot may be any one of the at least two spots.

According to an embodiment of the present disclosure, the processor 120 may measure the user body information using the voltage. As such, an existing touch screen may be used to reduce processing costs and to simplify the process.

According to an embodiment of the present disclosure, the processor 120 may compare the voltage with a preset first threshold voltage. The processor 120 may measure the user body information based on a result of the comparison. For example, the voltage sensed as the user's body portion contacts the touch screen by the first current induced across the user's body may be different from the voltage sensed as the user's body portion contacts the touch screen when the first current is not induced across the user's body.

Accordingly, the user body information may be measured by comparing the voltage sensed from the touch screen after the first current is induced across the user's body with the voltage sensed on the touch screen when the first current is not induced across the user's body. The processor 120 may measure the body information using a current in a similar manner to using the voltage.

According to an embodiment of the present disclosure, the first threshold voltage for the comparison may be set to a voltage sensed as the user's body portion contacts one of at least two spots on the touch screen before the power is applied to the first coil. For example, the processor 120 may set the first threshold voltage to the voltage measured as the user's body portion contacts the touch screen before the first current is induced across the user's body, which is before the power is applied to the first coil. The processor 120 may set a voltage corresponding to the user input to the first threshold voltage.

According to an embodiment of the present disclosure, the processor 120 may apply the first current to the user's body through an electrode included in the electronic device 101 when detecting the contact of the user's body portion on the touch screen. The electrode may be disposed outside the electronic device 101 and may directly contact the user's body to apply the first current to the user's body. For example, the electrode may be disposed at a portion that contacts the user's body in a device that may be worn by the user, such as a wearable device. However, the electrode may be disposed at a portion that contacts the user's body so that it is not externally exposed when the user wears the wearable device. The processor 120 may apply the first current to the user's body through the electrode corresponding to the user input.

According to an embodiment of the present disclosure, the processor 120 may measure the second current induced across the first coil included in the electronic device by the first magnetic field generated by the first current. As the first current is applied to the user's body by the electrode and flows across the user's body, the first magnetic field may be generated. The second current may be induced across the first coil in the electronic device 101 by the first magnetic field pursuant to the electromagnetic induction law, and the processor 120 may measure the second current. The first coil may be formed of a transparent film as described above and may be inserted in the electronic device 101.

According to an embodiment of the present disclosure, the processor 120 may measure the user body information using the second current. As described above, a portion of a human body may be an impedance and electrolyte, and the current and voltage of the user's body may be varied depending on the body fat, protein, minerals, bones, or muscles of the body.

Thus, the first current applied to the user's body and the second current induced across the first coil may be rendered to differ from each other, and the user body information may be measured using the second current and the first current. For example, the processor 120 may calculate the difference between the second current and the first current and may measure the user body information using the calculated difference.

According to an embodiment of the present disclosure, the processor 120 may detect a contact of the user's body in at least one predetermined area of the touch screen. For example, when the contact of the user's body on the area where the first coil is disposed is identified but not on the area where the second coil is disposed, the measurement of user body information might not properly be done. Accordingly, the processor 120 may detect the contact of the user's body in a predetermined area in order to more precisely measure the user body information.

According to an embodiment of the present disclosure, the processor 120 may output the predetermined area. For example, the predetermined area may be output to the touch screen through a user interface (UI), so that the user may intuitively recognize the predetermined area to easily measure the body information. The processor 120 may display the predetermined area on the touch screen through various user experiences (UXs) in various manners and may display the measured body information in various ways to provide the same to the user.

According to an embodiment of the present disclosure, the processor 120 may identify the area of the contact of the user's body and may compensate for the measured user body information based on the identified contact area. The magnitude of current induced across the user's body may be varied depending on the area of the contact of the user's body on the touch screen of the electronic device 101. For example, as the contact area increases, the current induced across the user's body may increase, and as the contact area decreases, the current induced across the user's body may decrease.

Accordingly, the user body information may be differently measured for the same user according to the identified contact area, and the accuracy of the user body information provided to the user may be reduced. Thus, in order to increase the accuracy of the user body information, the processor 120 may compensate for the measured user body information based on the identified contact area.

For example, a first contact area, which is a reference for measuring the user body information, may be set. When the identified contact area is larger than the first contact area, the current induced across the user's body may be larger than the induced current corresponding to the first contact area. In contrast, when the identified contact area is smaller than the first contact area, the current induced across the user's body may be smaller than the induced current corresponding to the first contact area.

As such, the processor 120 may identify the difference between currents induced across the user's body by the difference between the identified contact area and the first contact area. Further, the processor 120 may more precisely provide the user body information to the user by compensating for the measured user body information based on the identified difference in current. Further, it will be apparent to one of ordinary skill in the art that there may be applied various methods for compensating for the user body information according to the identified contact area by an algorithm for measuring the user body information.

According to an embodiment of the present disclosure, the processor 120 may measure at least one of a current and voltage induced across a coil embedded in the electronic device 101 by a magnetic field generated from outside of the electronic device 101. The processor 120 may select one of an operation of measuring body information or an operation of charging the electronic device 101 based on the measured current and voltage.

For example, the processor 120 may select one of the body information measuring operation or the charging operation based on at least one of an obtained user input, running a charging-related application, the magnitude of a current and voltage induced across the coil, and the magnitude of impedance measured by the current and voltage.

Figure 2:
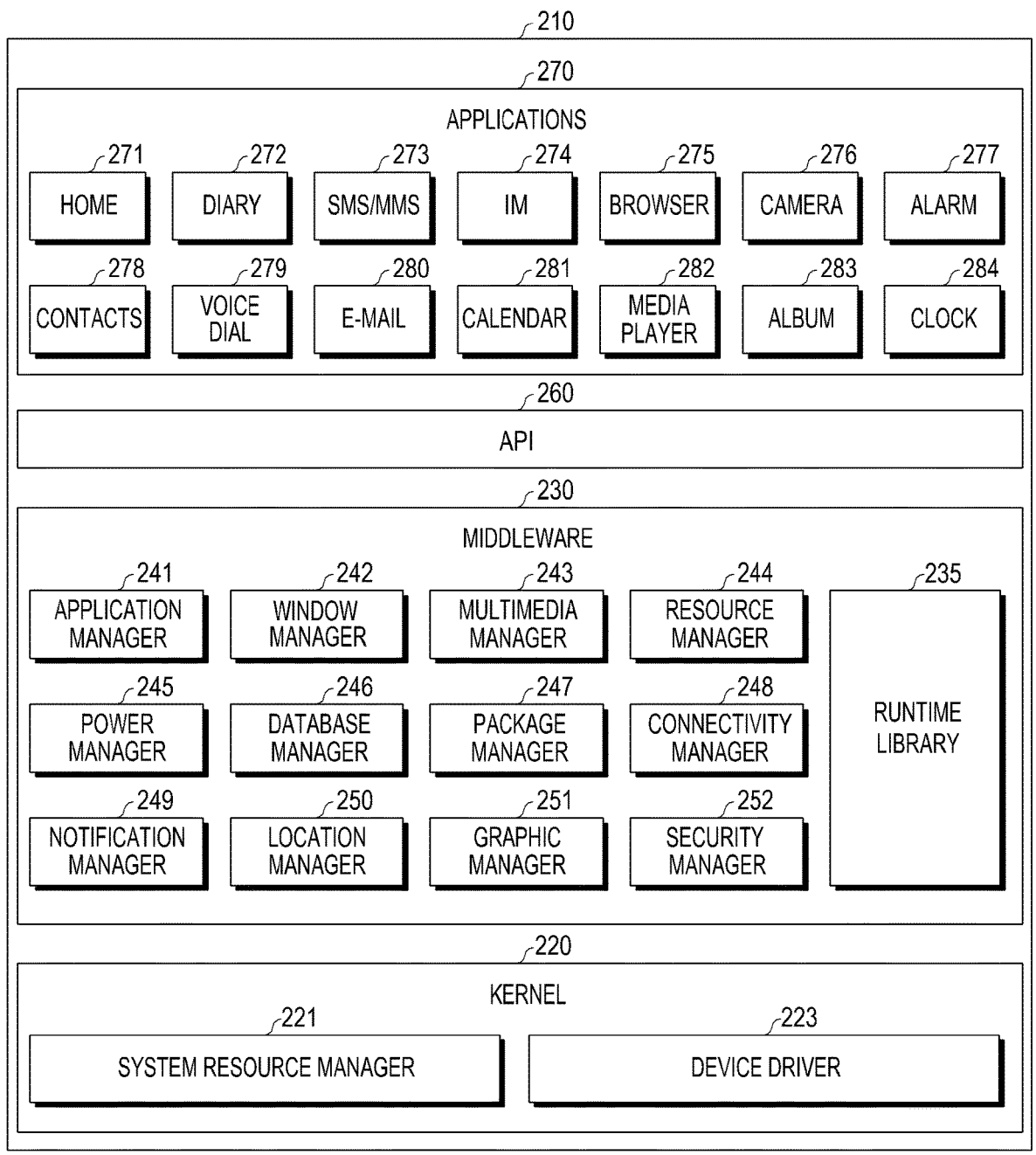
FIG. 2 is a block diagram illustrating a program module according to an embodiment of the present disclosure.

FIG. 2 is a block diagram illustrating a program module according to an embodiment of the present disclosure.

Referring to FIG. 2, a program module 210 (e.g., the program 140) may include an OS controlling resources related to the electronic device (e.g., the electronic device 101) and/or various applications (e.g., the AP 147) driven on the OS. The OS may include, e.g., Android, iOS, Windows, Symbian, Tizen, or Bada.

The program 210 may include, e.g., a kernel 220, middleware 230, an API 260, and/or an application 270. At least a part of the program module 210 may be preloaded on the electronic device or may be downloaded from an external electronic device (e.g., the electronic devices 102 and 104 or server 106).

The kernel 220 (e.g., the kernel 141) may include, e.g., a system resource manager 221 and/or a device driver 223. The system resource manager 221 may perform control, allocation, or recovery of system resources. According to an embodiment of the present disclosure, the system resource manager 221 may include a process managing unit, a memory managing unit, or a file system managing unit. The device driver 223 may include, e.g., a display driver, a camera driver, a Bluetooth driver, a shared memory driver, a USB driver, a keypad driver, a Wi-Fi driver, an audio driver, or an inter-process communication (IPC) driver.

The middleware 230 may provide various functions to the application 270 through the API 260 so that the application 270 may efficiently use limited system resources in the electronic device or provide functions jointly required by applications 270. According to an embodiment of the present disclosure, the middleware 230 (e.g., middleware 143) may include at least one of a runtime library 235, an application manager 241, a window manager 242, a multimedia manager 243, a resource manager 244, a power manager 245, a database manager 246, a package manager 247, a connectivity manager 248, a notification manager 249, a location manager 250, a graphic manager 251, or a security manager 252.

The runtime library 235 may include a library module used by a compiler in order to add a new function through a programming language while, e.g., the application 270 is being executed. The runtime library 235 may perform input/output management, memory management, or operation on arithmetic functions.

The application manager 241 may manage the life cycle of at least one application of, e.g., the applications 270. The window manager 242 may manage graphical user interface (GUI) resources used on the screen. The multimedia manager 243 may grasp formats necessary to play various media files and use a codec appropriate for a format to perform encoding or decoding on media files. The resource manager 244 may manage resources, such as source code of at least one of the applications 270, memory or storage space.

The power manager 245 may operate together with, e.g., a basic input/output system (BIOS) to manage battery or power and provide power information necessary for operating the electronic device. The database manager 246 may generate, search, or vary a database to be used in at least one of the applications 270. The package manager 247 may manage installation or update of an application that is distributed in the form of a package file.

The connectivity manager 248 may manage wireless connectivity, such as, e.g., Wi-Fi or Bluetooth. The notification manager 249 may display or notify an event, such as a coming message, appointment, or proximity notification, of the user without interfering with the user. The location manager 250 may manage locational information on the electronic device. The graphic manager 251 may manage graphic effects to be offered to the user and their related UI. The security manager 252 may provide various security functions necessary for system security or user authentication. According to an embodiment of the present disclosure, when the electronic device (e.g., the electronic device 101) has telephony capability, the middleware 230 may further include a telephony manager for managing voice call or video call functions of the electronic device.

The middleware 230 may include a middleware module forming a combination of various functions of the above-described components. The middleware 230 may provide a specified module per type of the OS in order to provide a differentiated function. Further, the middleware 230 may dynamically omit some existing components or add new components.

The API 260 (e.g., the API 145) may be a set of, e.g., API programming functions and may have different configurations depending on OSs. For example, in the case of Android or iOS, one API set may be provided per platform, and in the case of Tizen, two or more API sets may be offered per platform.

The application 270 (e.g., the application program 147) may include one or more applications that may provide functions such as, e.g., a home 271, a diary 272, a short message service (SMS)/multimedia messaging service (MMS) 273, an instant message (IM) 274, a browser 275, a camera 276, an alarm 277, a contact 278, a voice dial 279, an email 280, a calendar 281, a media player 282, an album 283, or a clock 284, a health-care (e.g., measuring the degree of workout or blood sugar), or provision of environmental information (e.g., provision of air pressure, moisture, or temperature information).

According to an embodiment of the present disclosure, the application 270 may include an application (hereinafter, "information exchanging application" for convenience) supporting information exchange between the electronic device (e.g., the electronic device 101) and an external electronic device (e.g., the electronic devices 102 and 104). Examples of the information exchange application may include, but are not limited to, a notification relay application for transferring specific information to the external electronic device, or a device management application for managing the external electronic device.

For example, the notification relay application may include a function for relaying notification information generated from other applications of the electronic device (e.g., the short message service (SMS)/multimedia messaging service (MIMS) application, email application, health-care application, or environmental information application) to the external electronic device (e.g., the electronic devices 102 and 104). Further, the notification relay application may receive notification information from, e.g., the external electronic device and may provide the received notification information to the user.

The device management application may perform at least some functions of the external electronic device (e.g., the electronic device 102 or 104) communicating with the electronic device (for example, turning on/off the external electronic device (or some components of the external electronic device) or control of brightness (or resolution) of the display), and the device management application may manage (e.g., install, delete, or update) an application operating in the external electronic device or a service (e.g., call service or message service) provided from the external electronic device.

According to an embodiment of the present disclosure, the application 270 may include an application (e.g., a health-care application of a mobile medical device) designated according to an attribute of the external electronic device (e.g., the electronic devices 102 and 104). According to an embodiment of the present disclosure, the application 270 may include an application received from the external electronic device (e.g., the server 106 or electronic devices 102 and 104). According to an embodiment of the present disclosure, the application 270 may include a preloaded application or a third party application downloadable from a server. The names of the components of the program module 210 according to the shown embodiment may be varied depending on the type of OS.

According to an embodiment of the present disclosure, at least a part of the program module 210 may be implemented in software, firmware, hardware, or in a combination of two or more thereof. At least a part of the programming module 210 may be implemented (e.g., executed) by e.g., a processor (e.g., the processor 210). At least a part of the program module 210 may include e.g., a module, a program, a routine, a set of instructions, a process, or the like for performing one or more functions.

Figure 3:
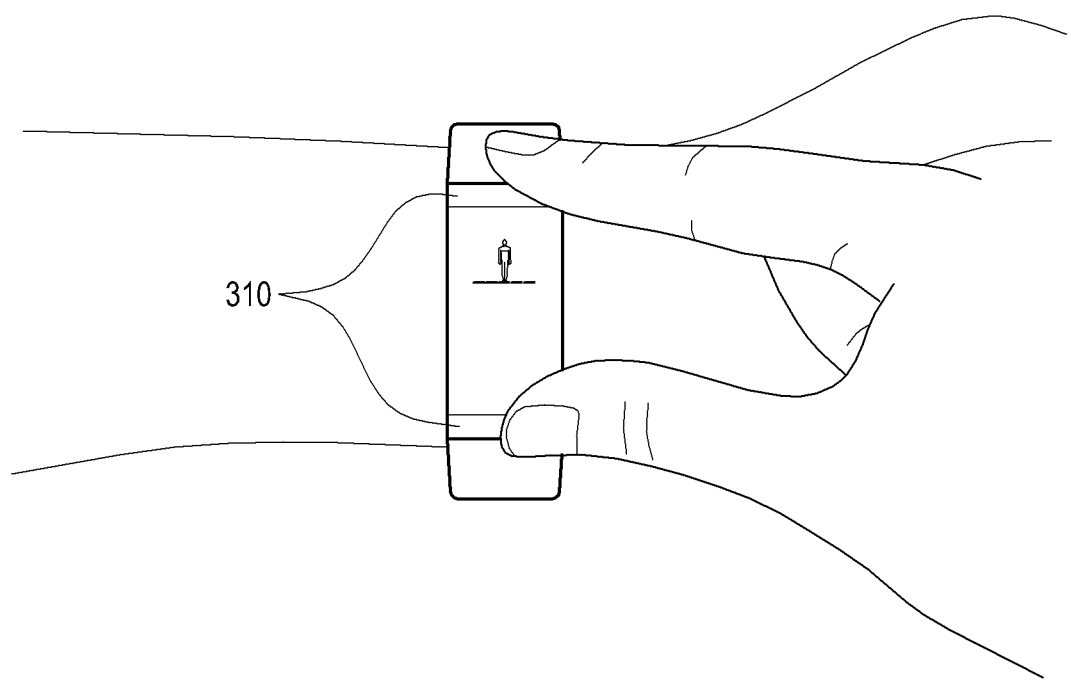
FIG. 3 is a view illustrating an electronic device for measuring body information according to the related art.

FIG. 3 is a view illustrating an electronic device for measuring body information according to the related art.

According to the related art, user body information is measured using electrodes disposed outside the electronic device. According to the related art, as methods for measuring user body information using the electrode, a two-electrode method or four-electrode method is used, wherein, in the two-electrode method, the same electrode is used without differentiating between a current electrode for applying current to the human body and a voltage electrode for measuring the human body impedance, while in the four-electrode method such current electrode and voltage electrode are separately used.

As such, according to the related art, the electrodes are difficult to embed in the electronic device, and thus, the electrodes are disposed outside the electronic device to measure user body information. This may degrade the look of the wearable device or mobile device. Further, the user's body should directly contact the electrode, increasing the risk of electric shock and germ contamination.

Referring to FIG. 3, two electrodes 310 are disposed outside the wearable device, harming the appearance and design of the wearable device. Further, as shown in FIG. 3, the user must directly touch his finger or fingers to the electrodes to measure user body information, resulting in an increased risk of electric shocks and germ contamination.

Figure 4A:
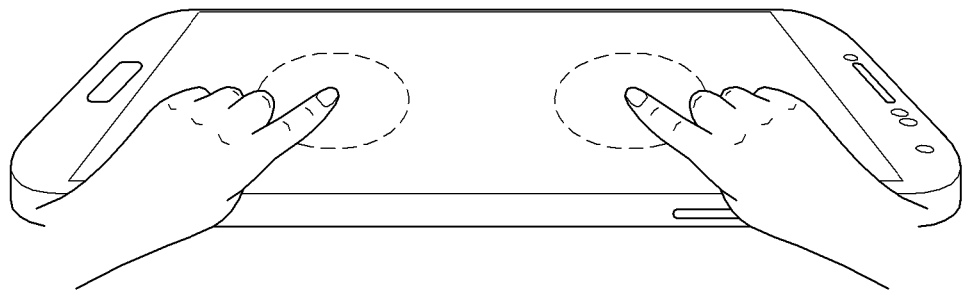
FIGS. 4A to 4C are views illustrating an electronic device for measuring information regarding a user's body according to an embodiment of the present disclosure.
Figure 4B:
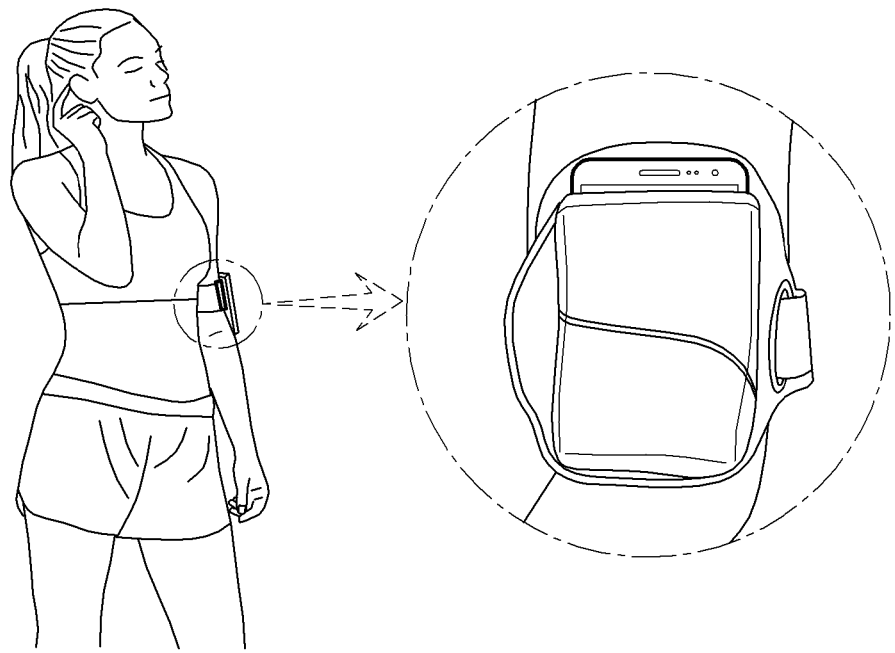
Figure 4C:
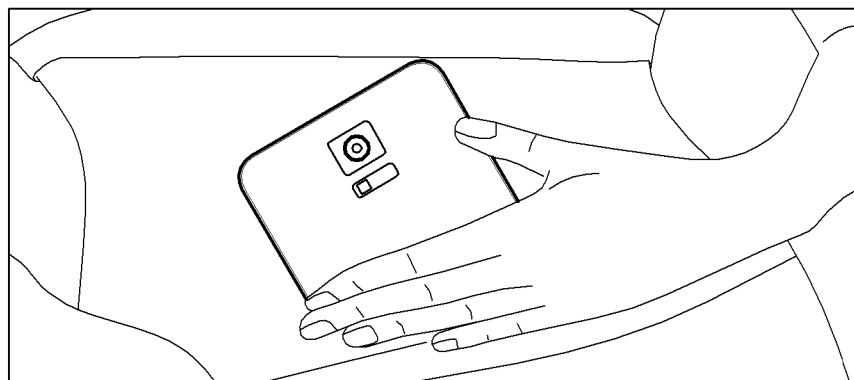

FIGS. 4A to 4C are views illustrating an electronic device for measuring information regarding a user's body according to an embodiment of the present disclosure.

According to an embodiment of the present disclosure, the electronic device 101 may measure user body information using at least one coil included in the electronic device 101. As such, the electronic device 101 may eliminate the need of direct contact between the user's body and the electrodes by measuring the user body information using the coil embedded in the electronic device 101. Accordingly, the risk of electric shocks and germ contamination may be reduced, without affecting the appearance and design of the electronic device 101.

Referring to FIG. 4A, the user may measure information regarding the whole body of the user by touching his finger at two spots on the touch screen. A current is induced across the user's body by a magnetic field generated by the coil embedded in the electronic device (e.g., electronic device 101), and a magnetic field may be generated by the current induced across the user's body. The user body information may be measured by measuring a current induced across another coil embedded in the electronic device 101 by the magnetic field generated by the current induced across the user's body. As such, when the user touches his finger at two predetermined spots as shown in FIG. 4A, the electronic device 101 may measure the information on the overall body of the user.

Not only may the user measure the information regarding his whole body but also the user may distinctively measure information regarding his upper body or information regarding his lower body by touching this finger at the two predetermined spots on the touch screen of the electronic device 101. The electronic device 101 may output the information regarding the user's upper body or the information regarding the user's lower body separately from the information regarding the whole body of the user.

Various body portions of the user may be used as touched on the touch screen to measure the user body information. For example, the body portion may be the user's wrist, palm, back of a hand, thigh, calf, shoulder, elbow, heel, sole, top of a foot, ankle, waste, flank, back, buttocks, knee, neck, chick, chin, forehead or other facial portion, etc.

According to an embodiment of the present disclosure, when the user's body portion touches at least two spots on the touch screen of the electronic device, body information may be measured. The two spots may be portions where the first coil and the second coil respectively are positioned or two portions of the touch screen where the first coil is positioned or two portions of the touch screen where the second coil is disposed. The two spots may be positioned over the portion of the touch screen where the first and second coils are positioned. The two spots may be guided to the predetermined area through the touch screen. The two spots may be two portions or points recognized when the user unconsciously touch his body portion on the touch screen.

Referring to FIGS. 4B and 4C, when the user's body portion, e.g., arm, stomach, and leg, contacts the touch screen of the electronic device 101, information regarding the arm, stomach, and leg may be measured. As such, when only a portion of the body contacts a portion of the touch screen of the electronic device 101, information regarding the portion of the body (also referred to as partial information) may be measured.

Figure 5:
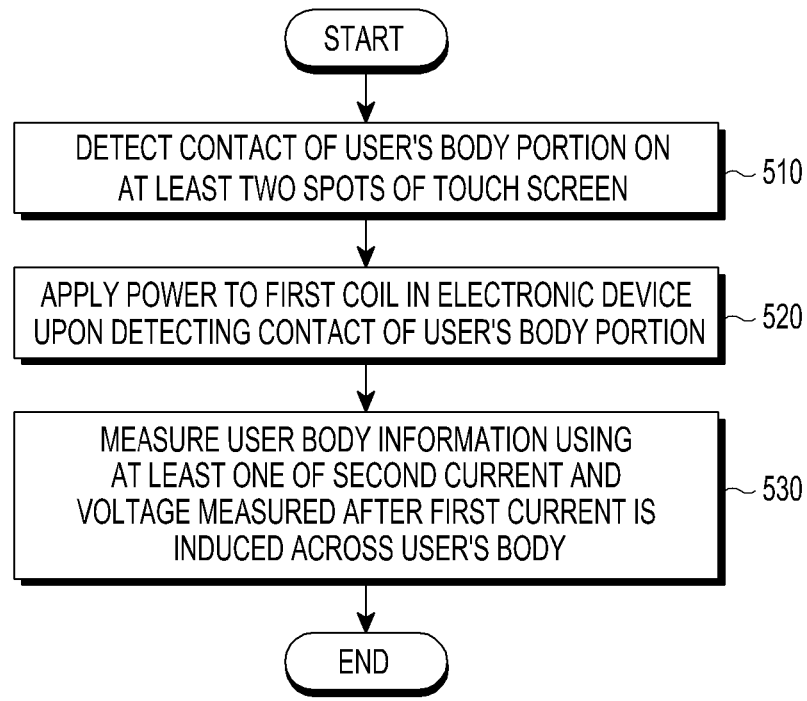
FIG. 5 is a flowchart illustrating a method for measuring information regarding a user's body through an electromagnetic induction method by an electronic device according to an embodiment of the present disclosure.

FIG. 5 is a flowchart illustrating a method for measuring user body information by an electronic device according to an embodiment of the present disclosure.

Referring to FIG. 5, the electronic device (e.g., the electronic device 101) may detect the contact of the user's body portion on at least, two spots of the touch screen in operation 510. For example, the electronic device 101 may detect the contact of the user's body portion by identifying at least one of the area, position, and time of the contact of the user's body portion.

In operation 520, when detecting the contact of the user's body portion on at least two spots of the touch screen, the electronic device 101 may apply power to the first coil in the electronic device. The electronic device 101 may apply the power as the contact of the user's body is detected or may detect the contact of the user's body while the power is applied. For example, operation 520 may be performed after operation 510, or operation 510 may be performed after operation 520.

The first coil may be processed in the form of a transparent film and may be inserted in the electronic device 101. As the first coil is inserted in the electronic device 101, the first coil might not be viewed from outside. When the power is applied to the first coil, the first magnetic field may be generated by the electromagnetic induction law.

The power applied to the first coil may be DC power or AC power. The alternating period of the current may be previously set so that the first magnetic field may have a predetermined frequency.

In operation 530, the electronic device 101 may measure the user body information using at least one of the second current and voltage measured after the first current is induced across the user's body by the first magnetic field. The electronic device 101 may identify the contact area of the user's body and compensate or adjust the measured body information based on the identified contact area.

The electronic device 101 may output the user body information on the touch screen. A more specific method for measuring the user body information using the measured second current and voltage by the electronic device 101 is described below.

Figure 6:
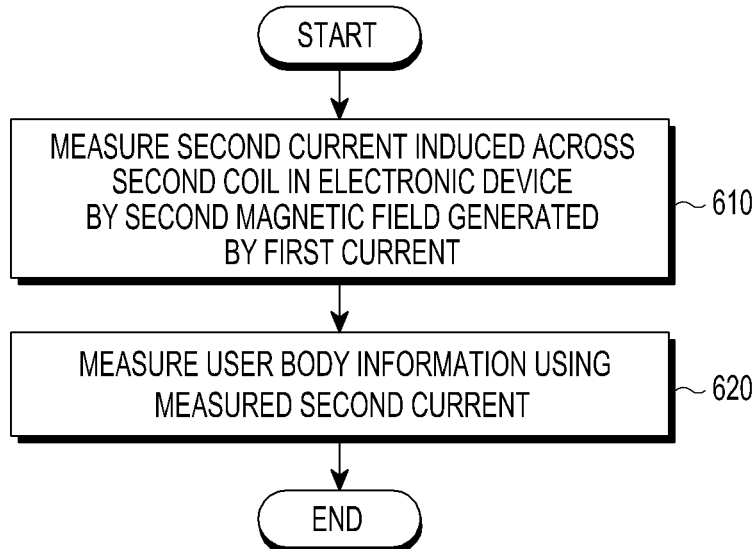
FIG. 6 is a flowchart illustrating a method for outputting information regarding a user's body through an electromagnetic induction method by an electronic device according to an embodiment of the present disclosure.

FIG. 6 is a flowchart illustrating a method for outputting information regarding a user's body through an electromagnetic induction method by an electronic device according to an embodiment of the present disclosure.

Referring to FIG. 6, the electronic device 101 may measure the second current induced across the second coil in the electronic device 101 by the second magnetic field generated by the first current induced across the user's body in operation 610. As the first current is induced across the user's body, the second magnetic field may be generated by the induced first current.

The electronic device 101 may measure the second current induced across the second coil in the electronic device 101 by the second magnetic field generated by the first current.

The second coil may also be formed of a transparent film like the first coil described above in connection with FIG. 5 and may be inserted in the electronic device 101. The first coil and the second coil may be included in the same transparent film. For example, the first coil and the second coil may be processed to be disposed in at least some areas, respectively, of the transparent film. The first coil and the second coil may be wound in different directions, and accordingly, the magnetic fields generated when power is applied to the first coil and the second coil may have different directions.

Like the first coil, the second coil may be formed as an air-core coil or core-type coil depending on components and may be shaped as a spiral, ring, loop, or meander depending on its shape. The first coil and the second coil may be configured with the same component or the same shape or may be configured with different coil shapes or components by a method providing easier measurement of body information.

In operation 620, the electronic device 101 may measure user body information using the measured second current. A portion of a human body may be an impedance and electrolyte, and current and voltage may be varied depending on the body fat, protein, minerals, bones, or muscles of the body.

Accordingly, the current flowing across the first coil to generate the first magnetic field may be different from the second current induced across the second coil by the second magnetic field generated by the first current. Thus, the electronic device 101 may measure the user body information using the second current and the current flowing across the first coil. For example, the processor 120 may calculate the difference between the second current induced across the second coil and the current flowing across the first coil as the power is supplied to measure the user body information.

The method for measuring the user body information based on the second current induced across the second coil may adopt different measurement algorithms depending on types of the user body information. For example, for body fat information, a predetermined body fat measurement algorithm may apply which measures body fat using the measured second current. Likewise, for muscle information, a predetermined muscle measurement algorithm may apply which measures muscles using the measured second current. The algorithms for measuring each type of user body information based on the measured second current is apparent to one of ordinary skill in the art, and its detailed description is skipped.

Figure 7:
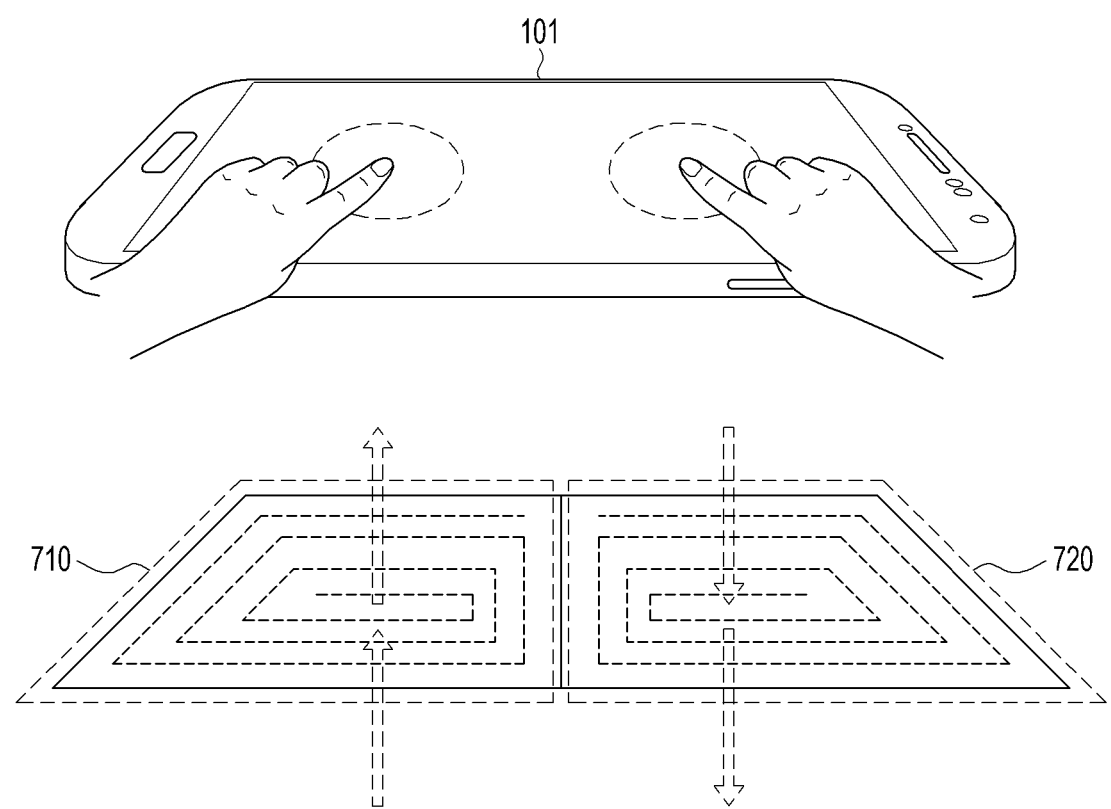
FIG. 7 is a view illustrating a method for measuring body information through an electromagnetic induction method by an electronic device according to an embodiment of the present disclosure.

FIG. 7 is a view illustrating a method for measuring body information through an electromagnetic induction method by an electronic device according to an embodiment of the present disclosure.

Referring to FIG. 7, a loop-type first coil 710 and a loop-type second coil 720 may be processed to be disposed in one transparent film. The first coil 710 and the second coil 720 may be processed to have opposite directions of coil windings, and accordingly, the magnetic fields may be generated in opposite directions from the first coil 710 and the second coil 720.

For example, the magnetic field generated by the first coil 710 may be oriented from inside of the electronic device 101 to the touch screen. In contrast, the magnetic field generated by the second coil 720 may be oriented from the touch screen of the electronic device 101 to the inside of the electronic device 101.

As the first coil 710 and the second coil 720 have more turns, the measurement rate of body information may increase. As the turn count of the coil increases, its resultant magnetic field may be further intensified, leading to an increased measurement rate of the body information.

As shown in FIG. 7, the first coil 710, in which the generated magnetic field is directed from inside of the electronic device 101 to the touch screen, may be operated as a source coil to which power is applied in order to induce current across the user's body. The second coil 720, in which the generated magnetic field is directed from the touch screen of the electronic device 101 to the inside, may be operated as a reception coil where current and voltage are induced by a magnetic field generated by the current flowing across the user's body.

The touch panel may sense the user's touch input and output a touch event value corresponding to the sensed touch signal. When the touch panel is combined with the display panel to configure the touch screen (not shown), the touch screen may be implemented with various types of touch sensors, such as in a capacitive, resistive, or piezoelectric type. In the capacitive type, a tiny amount of electricity created when the user's body portion touches the touch screen using a dielectric coated on the touch screen may be detected to compute the coordinate of the touch. In the resistive type, a current flow generated when two electrode plates embedded in the touch screen come in contact at the touched spot as the user touches the screen may be sensed to compute the coordinate of the touch. The touch event generated on the touch screen may be generated primarily by the user's finger or may also be generated by an object formed of a conductive material that may cause a change in capacitance.

The pen recognition panel may detect a proximity input or touch input by a touch pen (e.g., stylus pen or digitizer pen) of the user and output the detected pen proximity event or pen touch event. The pen recognition panel may be implemented, e.g., in an electromagnetic resonance (EMR) type and may sense a touch or proximity input by a change in electromagnetic field due to the approach or touch of the pen. For example, the pen recognition panel may include electromagnetic induction coil sensors (not shown) having a grid structure and an electronic signal processor (not shown) sequentially providing AC signals of a predetermined frequency to the respective loops of the electromagnetic induction sensors. When a pen with a resonant circuit is present near the loop coil of the pen recognition panel, a magnetic field transmitted from the loop coil generates a current across the resonant circuit in the pen by mutual inductance. The coil of the resonant circuit in the pen induces a magnetic field based on the current, and the pen recognition panel detects the induced magnetic field from the loop coil that is in a signal reception state, allowing the position of pen approach or touch to be detected. The pen recognition panel may be prepared to have a predetermined area under the display panel, e.g., an area covering the display area of the display panel.

The first coil 710 and the second coil 720 may be processed to be disposed in one transparent film, and the transparent film may be inserted in the electronic device 101. For example, the transparent film may be processed to be disposed under the touch panel of the electronic device 101.

Accordingly, the transparent film may avoid external exposure such that direct contact with the user's body when measuring user body information is prevented.

As shown in FIG. 7, the user may receive the user body information measured using at least one of the current and voltage induced across the second coil 720 as the user's body portion contacts the touch screen of the electronic device 101. According to the related art, electrodes for measuring user body information, e.g., body fat, are disposed outside the body fat measuring device, and the user measures his body fat by touching the electrodes.

In contrast, according to an embodiment of the present disclosure, the electronic device 101 may induce the user to touch the touch screen to measure body information by utilizing various applications and may accordingly measure the body information and display the same on the touch screen.

Figure 8:
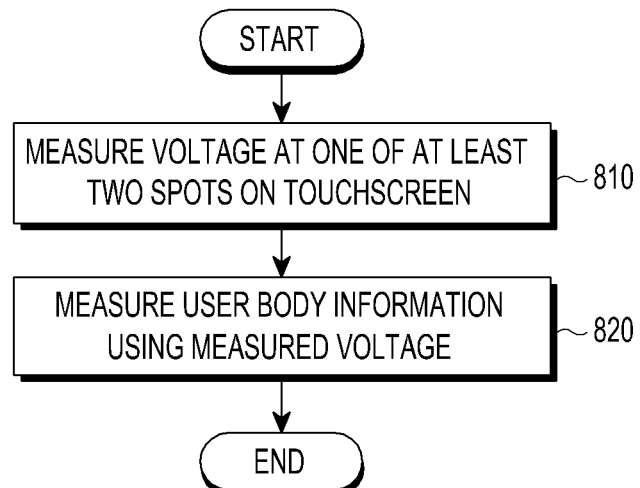
FIG. 8 is a flowchart illustrating a method for outputting information regarding a user's body through an electromagnetic induction method and capacitive method by an electronic device according to an embodiment of the present disclosure.

FIG. 8 is a flowchart illustrating a method for outputting information regarding a user's body through an electromagnetic induction method and capacitive method by an electronic device according to an embodiment of the present disclosure.

Referring to FIG. 8, the electronic device 101 may measure voltage at one of at least two spots on the touch screen in operation 810. For example, the electronic device 101 may measure the voltage sensed on the touch screen as the user's body portion contacts the touch screen.

In operation 820, the electronic device 101 may measure the user body information using the measured voltage.

Unlike the method for measuring body information described above in connection with FIG. 6, the electronic device 101 may measure the user body information using the voltage sensed on the touch screen as the user's body portion contacts the touch screen as shown in FIG. 8. In this case, the electronic device 101 may include the first coil generating the first magnetic field but exclude the second coil described above in connection with FIG. 6. For example, the first coil may function as the source coil, and the touch screen may be used to measure, e.g., changes in current and voltage generated from the user's body as the reception coil does. For example, the electronic device 101 may measure the changes in current and voltage generated from the user's body using the magnitude or level of the voltage sensed on the touch screen.

As such, an existing touch screen may be used, saving processing costs while simplifying the process.

Figure 9:
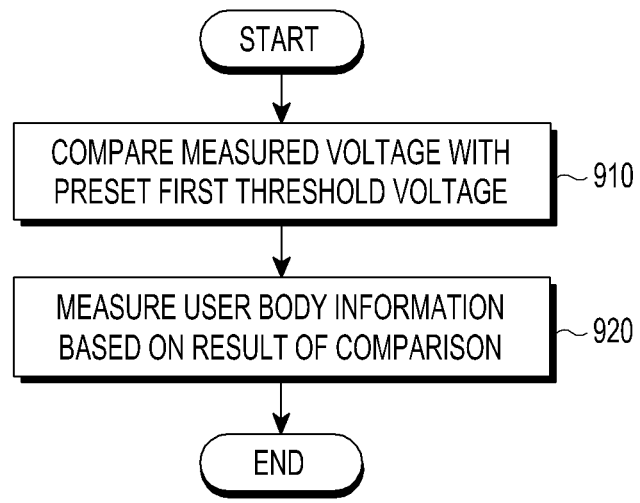
FIG. 9 is a flowchart illustrating a method for measuring information regarding a user's body using a voltage measured by an electronic device according to an embodiment of the present disclosure.

FIG. 9 is a flowchart illustrating a method for measuring information regarding a user's body using a voltage measured by an electronic device according to an embodiment of the present disclosure.

Referring to FIG. 9, the electronic device 101 may compare the voltage with a first threshold voltage in operation 910. The voltage sensed as the user's body portion contacts the touch screen by the first current induced across the user's body may be different from the voltage sensed as the user's body portion contacts the touch screen when the first current is not induced across the user's body.

Accordingly, the user body information may be measured by comparing the voltage sensed from the touch screen after the first current is induced across the user's body with the voltage sensed on the touch screen when the first current is not induced across the user's body.

The first threshold voltage may be set to a voltage sensed as the user's body portion contacts one of at least two spots on the touch screen before the power is applied to the first coil.

In operation 920, the electronic device 101 may measure the user body information based on the result of the comparison. As set forth above, since the voltage sensed on the touch screen makes a difference depending on whether current is induced across the user's body, the user body information may be measured based on the result of comparison. For example, a variation in voltage sensed on the touch screen generated as current is induced across the user's body may be obtained by the electronic device 101, and the user body information may be measured based on the obtained voltage variation.

Figure 10:
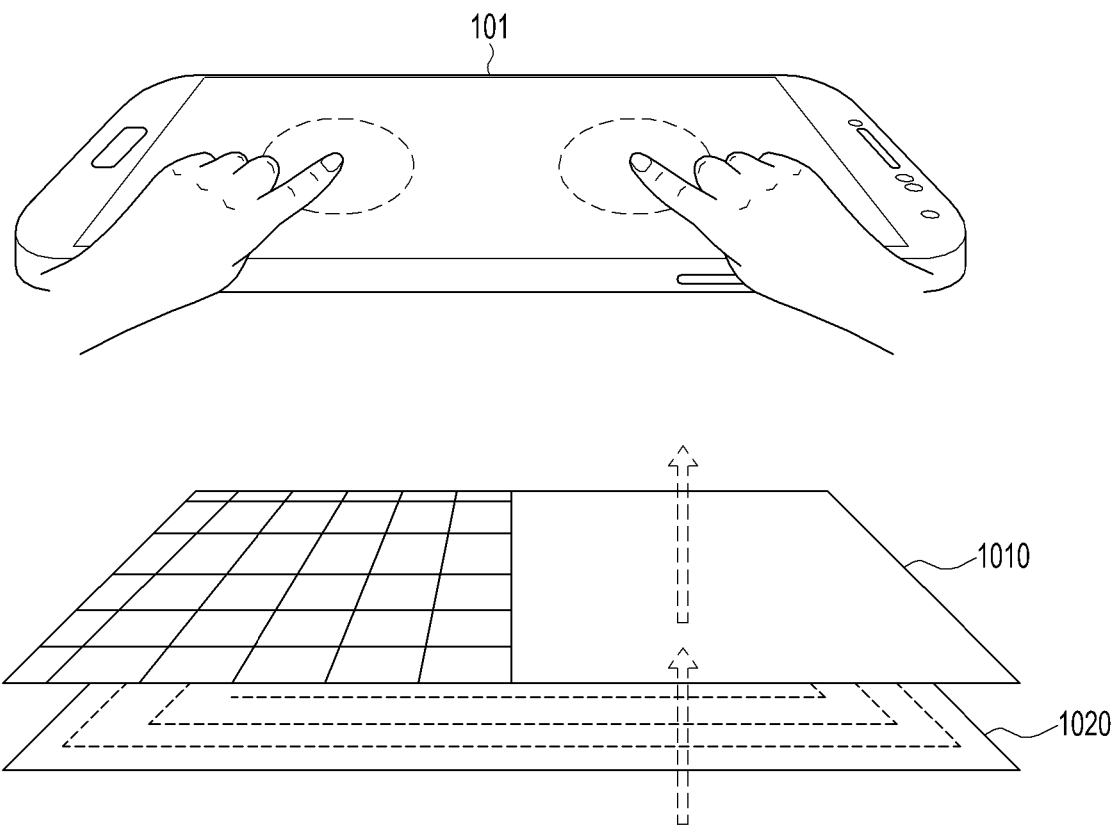
FIG. 10 is a view illustrating a method for measuring body information through a capacitive method and electromagnetic induction method by an electronic device according to an embodiment of the present disclosure.

FIG. 10 is a view illustrating a method for measuring body information through a capacitive method and electromagnetic induction method by an electronic device according to an embodiment of the present disclosure.

Referring to FIG. 10, a touch panel 1010 included in the touch screen may be used to measure, e.g., a variation in current and voltage sensed as the user's body portion contacts the same. A first coil 1020 may be processed to be disposed in a transparent film and may be operated as a source coil generating a magnetic field to induce current across the user's body. Thus, the magnetic field generated by the first coil 1020 may be oriented from inside of the electronic device 101 to the touch screen.

The first coil 1020 may be processed to be disposed under the touch panel 1010. Accordingly, the transparent film having the first coil 1020 disposed therein may avoid external exposure such that direct contact with the user's body when measuring user body information is prevented.

As shown in FIG. 10, the user may receive the user body information measured using the voltage sensed from the touch panel 1010 by touching his body portion to the touch screen of the electronic device 101. For example, the electronic device 101 may compare the voltage sensed on the touch panel 1010 with a first threshold voltage and may measure the user body information based on the result of the comparison.

Although not shown, the electronic device 101 may measure the voltage sensed as a touch pen contacts the touch screen to measure the user body information. For example, the voltage sensed as the touch pen contacts the touch screen in the pen recognition panel in the electronic device 101 as the first current is induced across the user's body may be different from the voltage sensed as the touch pen contacts the touch screen in the pen recognition panel when the first current is not induced. Accordingly, the electronic device 101 may measure the voltage sensed as a touch pen contacts the touch screen to measure the user body information.

Figure 11:
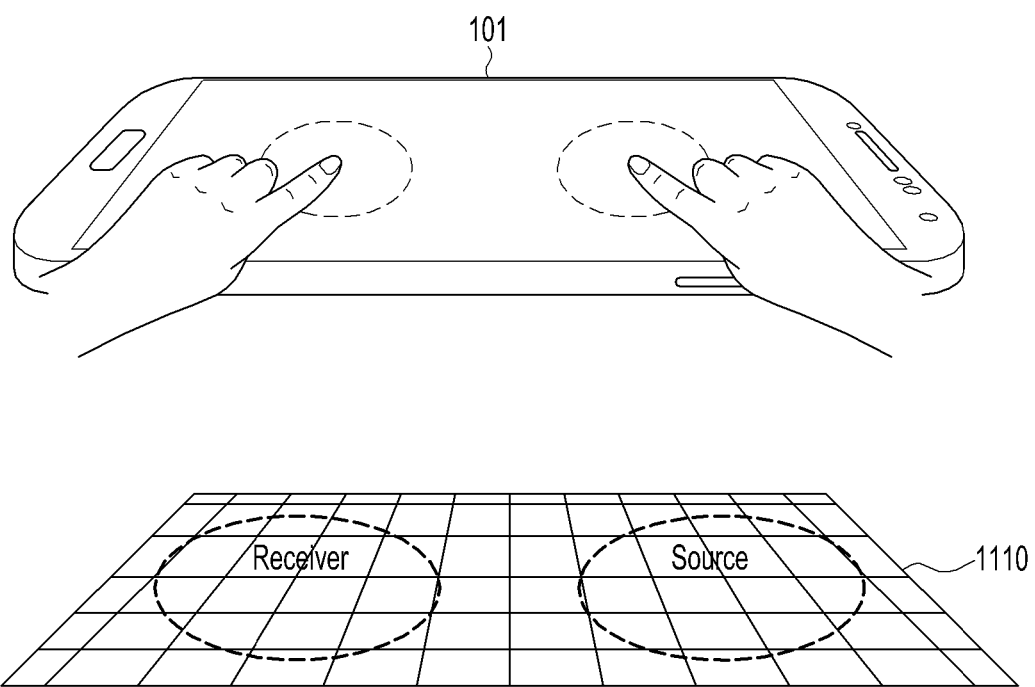
FIG. 11 is a view illustrating a method for measuring body information through a capacitive method by an electronic device according to an embodiment of the present disclosure.

FIG. 11 is a view illustrating a method for measuring body information through a capacitive method by an electronic device according to an embodiment of the present disclosure.

Referring to FIG. 11, according to an embodiment of the present disclosure, the electronic device 101 may measure user body information using a touch panel 1110 included in the touch screen of the electronic device 101 without using the first coil and second coil described above in connection with FIGS. 7 and 10.

For example, as shown in FIG. 11, the touch panel 1110 may be split into a first part and a second part, and the first part may be used as a source for applying current to the user's body while the second part may be used for measuring variations in current and voltage generated from the body.

In this case, since the existing touch panel 1110, which is included in the touch screen, is used, there is no need of additional hardware components. However, by the structural nature of the touch panel, the first part and the second part need to be sequentially controlled.

Accordingly, when the touch panel 1110 is used as shown in FIG. 11, the user is required to perform control to read and write horizontal or vertical patterns of lines depending on the situation where the user holds the UX or electronic device 101.

As such, even without using the coil included in the electronic device 101, the user body information may be measured with the touch panel included in the touch screen of the electronic device 101.

Figure 12:
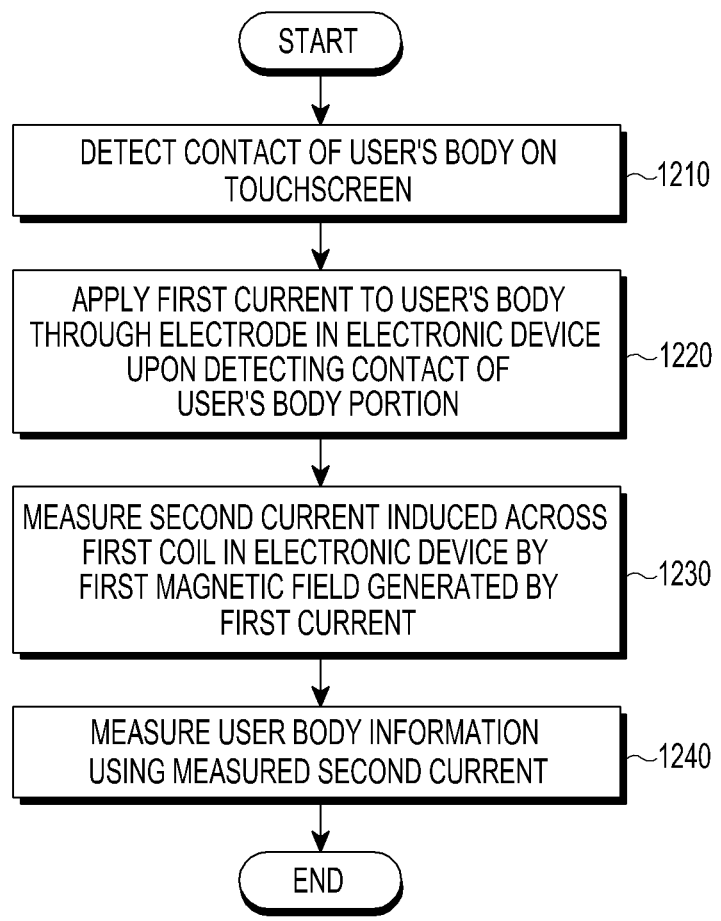
FIG. 12 is a flowchart illustrating a method for measuring information regarding a user's body through an electrode and electromagnetic induction method by an electronic device according to an embodiment of the present disclosure.

FIG. 12 is a flowchart illustrating a method for measuring information regarding a user's body through an electrode and electromagnetic induction method by an electronic device according to an embodiment of the present disclosure.

Referring to FIG. 12, the electronic device 101 may detect the contact of the user's body portion on at least two spots of the touch screen in operation 1210. For example, the electronic device 101 may detect the contact of the user's body portion by identifying at least one of the area, position, and time of the contact of the user's body portion.

In operation 1220, when detecting the contact of the user's body portion on at least two spots of the touch screen, the electronic device 101 may apply the first current to the user's body through electrodes included in the electronic device 101. The electronic device 101 may apply the power as the contact of the user's body is detected or may detect the contact of the user's body while the power is applied. For example, operation 1220 may be performed after operation 1210, or operation 1210 may be performed after operation 1220.

The electrodes may be formed of a material enabling current to flow across a conductor, e.g., a metal, carbon, alloy, oxide, or semiconductor. The electrodes may be disposed outside the electronic device 101 and may directly contact the user's body to apply the current to the user's body.

For example, the electrodes may be disposed at a portion that contacts the user's body in a device that may be worn by the user, such as a wearable device. For example, for a smartwatch, an example of the wearable device, the electrodes may be disposed on the strap, back cover or crown of the smartwatch.

Accordingly, the electronic device 101 may control the electrodes not to apply the first current whenever the user's body contacts the electrodes. For example, the electronic device 101 may apply the first current through the electrodes upon identifying that the user's body contacts the touch screen.

In operation 1230, the electronic device 101 may measure the second current induced across the first coil in the electronic device 101 by the first magnetic field generated by the first current. As the first current is applied to the user's body by the electrode and flows across the user's body, the first magnetic field may be generated. The electronic device 101 may measure the second current induced across the first coil by the first magnetic field under the electromagnetic induction law.

In operation 1240, the electronic device 101 may measure the user body information using the second current. For example, the electronic device 101 may calculate the difference between the second current and the first current and may measure the user body information based on the calculated difference.

Figure 13A:
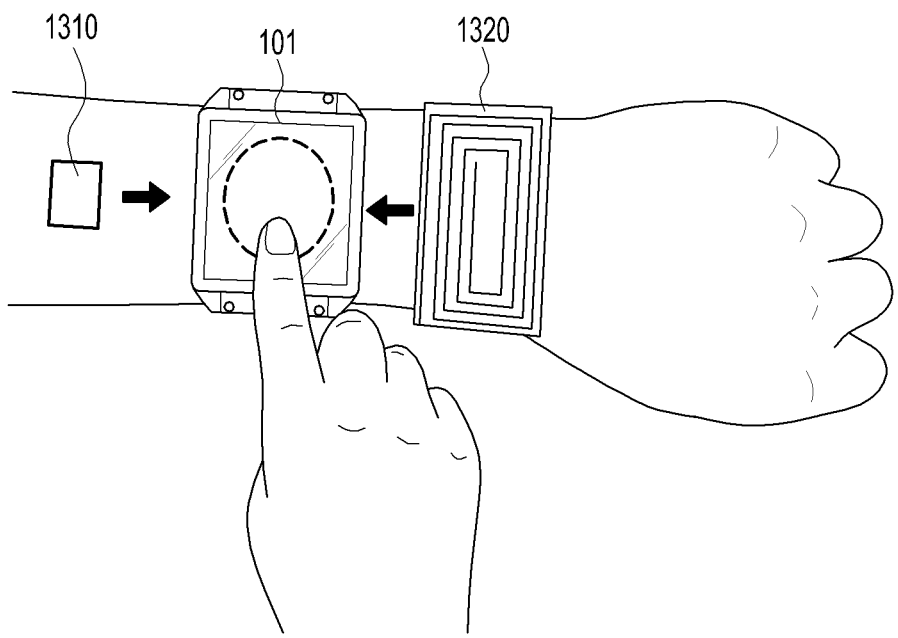
FIGS. 13A to 13C are views illustrating a structure of an electronic device for measuring information regarding a user's body through an electrode and electromagnetic induction method according to an embodiment of the present disclosure.
Figure 13B:
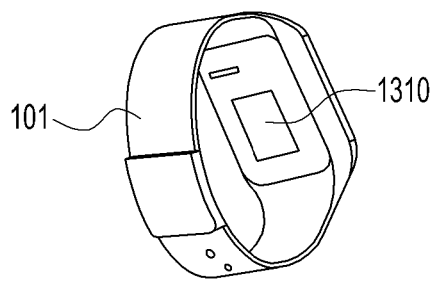
Figure 13C:
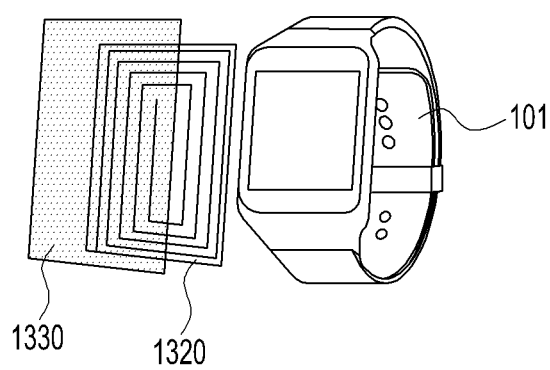

FIGS. 13A to 13C are views illustrating a structure of an electronic device for measuring information regarding a user's body through an electrode and electromagnetic induction method according to an embodiment of the present disclosure.

Referring to FIG. 13A, the electronic device 101 may be processed so that an electrode 1310 is disposed on a rear surface of the electronic device 101 and a first coil 1320 is disposed inside the electronic device 101.

For example, the electrode 1310 and the first coil 1320 may be arranged as shown in FIGS. 13B and 13C.

Referring to FIG. 13B, the electrode may be disposed on the rear surface of the electronic device 101, which comes in contact with the user's body. As the electrode is disposed on the rear surface of the electronic device 101, the electrode is not externally exposed when the use wears the electronic device 101.

The electronic device 101 may apply a current to the user's body using the electrode 1310 disposed on the rear surface of the electronic device 101. For example, the electronic device 101 may display a UX for inducing the user to touch his body through the touch screen. When the user sees the UX and touches the touch screen, the area where the electrode 1310 contacts the user's body, e.g., his wrist, increases, leading to efficient application of the current to the user's body.

The coil may be formed as an air-core coil or core-type coil and may be shaped as a spiral, ring, loop, or meander depending on its shape. The first coil 1320 may be formed of iron, molybdenum, nickel, silicon, aluminum, or a combination thereof. In the instant embodiment of the present disclosure, the first coil 1320 may be processed in the form of a transparent film and disposed under a touch panel 1330 to avoid harming the appearance of the electronic device 101.

Referring to FIG. 13C, the first coil 1320 may be processed in the form of a transparent film and disposed under the touch panel 1330. As such, the first coil 1320 may be disposed under the touch panel 1330 and may thus operate as a contactless electrode.

As such, the electronic device 101 may use the electrode 1310 in such an extent as not to significantly deteriorate the appearance. Although not shown, a component with a shielding functionality may be added to prevent a magnetic field that may be generated between the electrode 1310 and the first coil 1320. For example, a shielding sheet formed of a magnetic body may be disposed between the electrode 1310 and the first coil 1320.

As the permeability, area, and thickness of the magnetic body increase, the magnetic field shielding function may be enhanced. However, such method of shielding magnetic field between the electrode 1310 and the first coil 1320 through the shielding sheet is merely an example for achieving the goals of the present disclosure, and the present disclosure is not limited thereto. It will be apparent to one of ordinary skill in the art that various shielding methods may be adopted to shield magnetic field between the electrode 1310 and the first coil 1320.

The electronic device 101 uses the first coil 1320 and thus enables itself to use only one electrode as compared with approaches using multiple electrodes to measure, e.g., body fat, according to the related art.

According to an embodiment of the present disclosure, the electronic device 101 may use the first coil 1320 as a source coil. For example, the electronic device 101, rather than applying the first current to the user's body through the electrode 1310, may apply power to the first coil 1320 so that the first current flows across the user's body.

Accordingly, the electronic device 101 may configure the electrode 1310 as a voltage electrode for measuring the impedance of the user's body. Thus, the electronic device 101 may measure user body information using the impedance of the user's body measured through the electrode 1310.

Although not shown, the electronic device 101 may measure user body information using the touch panel 1330 included in the touch screen of the electronic device 101 and the electrode 1310 without using the first coil 1320.

For example, the touch panel may be used to measure variations in current and voltage generated from the user's body as described above in connection with FIG. 11. In this case, since the existing touch panel, which is included in the touch screen, is used, there is no need of additional hardware components. As such, user body information may be measured using the electrode 1310 and the touch panel.

Figure 14:
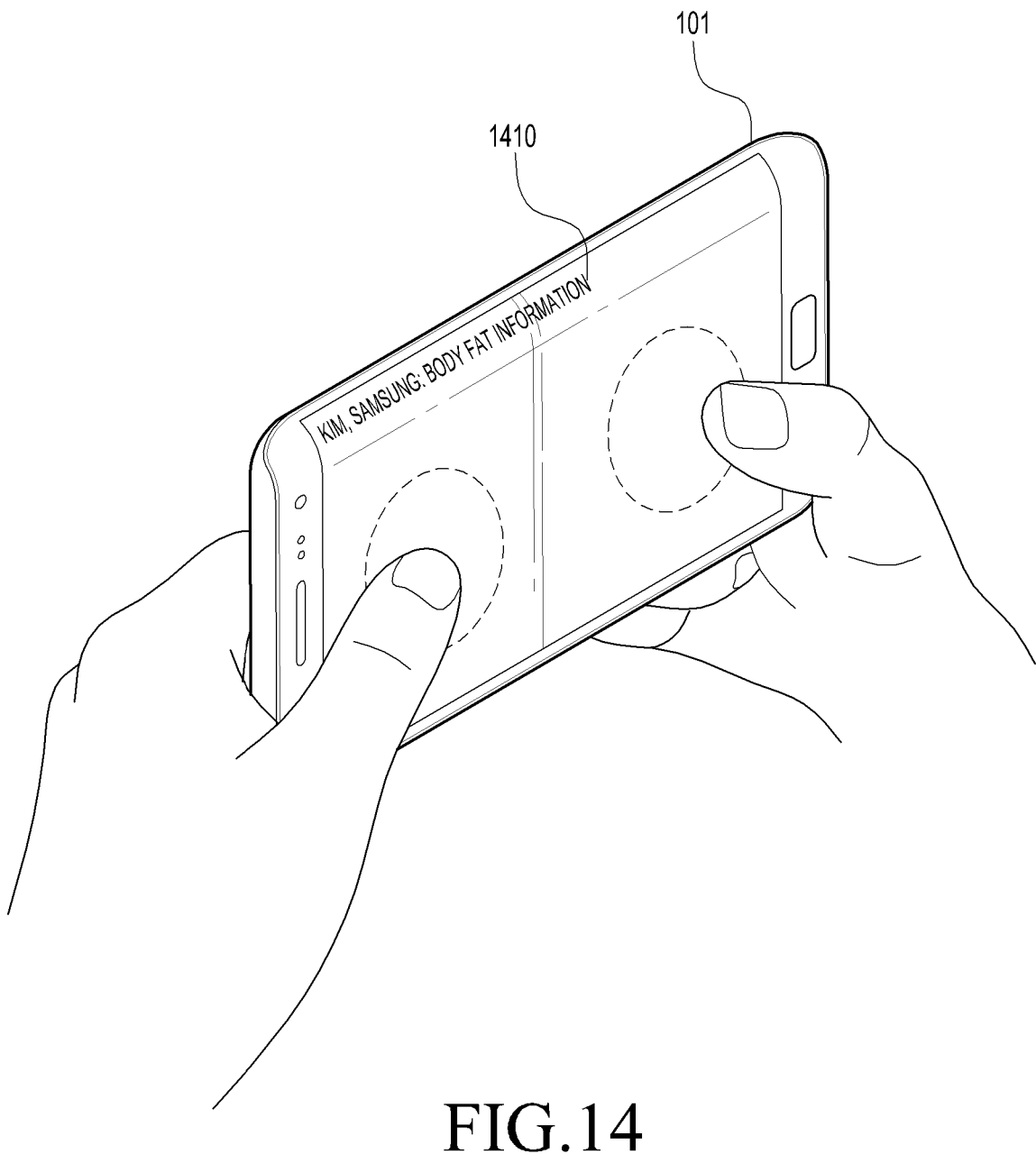
FIG. 14 is a view illustrating an electronic device for outputting body information measured according to an embodiment of the present disclosure.

FIG. 14 is a view illustrating an electronic device for outputting body information measured according to an embodiment of the present disclosure.

According to an embodiment of the present disclosure, the electronic device 101 may include at least one of a first coil and a second coil and use the first coil and second coil as contactless electrode as described above. The electronic device 101 may induce the user to touch his body through various UXs or UIs and may provide measured user body information.

Referring to FIG. 14, a UX for inducing the user to touch his body may be displayed on the touch screen of the electronic device 101. In order to allow the user to easily receive the user body information while maintaining the touch on the touch screen, the electronic device 101 may enable the measured user body information to be output on an edge area display 1410 of the touch screen. Accordingly, the user may receive the measured body information through the edge area display 1410.

Figure 15:
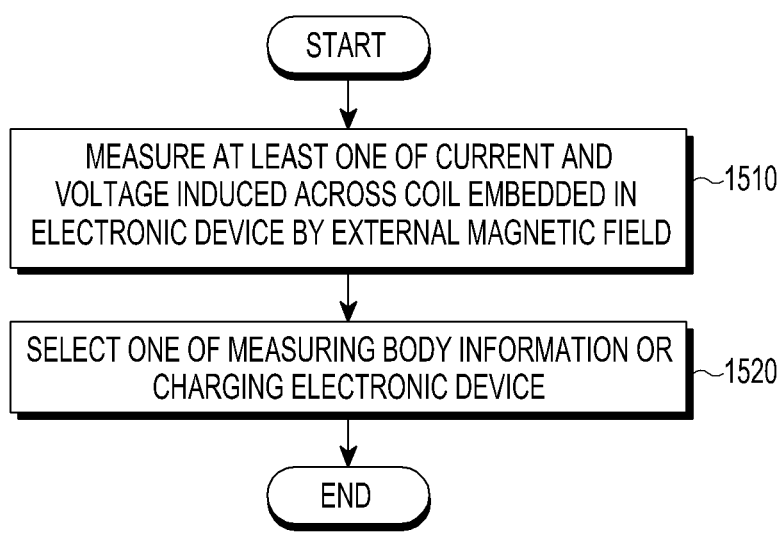
FIG. 15 is a flowchart illustrating a method for selecting one of body information measurement and wireless charging by an electronic device according to an embodiment of the present disclosure.

FIG. 15 is a flowchart illustrating a method for selecting one of body information measurement and wireless charging by an electronic device according to an embodiment of the present disclosure.

Referring to FIG. 15, the electronic device 101 may measure at least one of a current and voltage induced across a coil embedded in the electronic device 101 by an external magnetic field in operation 1510. At least one of a current and voltage may be induced across the coil by the magnetic field as per the electromagnetic induction law.

In an embodiment of the present disclosure, the external magnetic field may be generated outside the electronic device 101 and induce at least one of a current and voltage across the coil in the electronic device 101. For example, the external magnetic field may be a magnetic field that is generated by current flowing across the user's body or a magnetic field that is generated by current flowing across a device for wireless charging. As such, the external magnetic field may be generated outside the electronic device 101 and induce at least one of a current and voltage across the coil in the electronic device 101.

In operation 1520, the electronic device 101 may select one of an operation of measuring body information using at least one of the current and voltage or an operation of charging the electronic device using at least one of the current and voltage, based on at least one of the measured current and voltage.

For example, the electronic device 101 may select one of the body information measuring operation or the charging operation based on at least one of an obtained user input, running a charging-related application, the magnitude of a current and voltage induced across the coil, and the magnitude of impedance measured by the current and voltage.

For example, the electronic device 101 may charge the electronic device 101 without measuring the user body information according to the user input. When the charging-related application runs, the electronic device 101 may automatically charge the electronic device 101. In contrast, when an application related to measuring the body information runs, the electronic device 101 may automatically measure the body information.

The electronic device 101 may identify the load generating the external magnetic field according to the magnitude of the current and voltage induced across the coil. For example, the processor 120 may previously measure the magnitude of current and voltage induced by a magnetic field generated by a wireless charger and measure the magnitude of current and voltage induced by a magnetic field generated by the human body. The electronic device 101 may identify the load based on the magnitude of current and voltage previously measured, and when the load is identified to be the human body, may measure the user body information. In contrast, the electronic device 101, when the load is identified to be the wireless charger, may charge the electronic device 101.

Likewise, the electronic device 101 may identify the load generating the external magnetic field according to the magnitude of impedance measured by the current and voltage induced across the coil. For example, when the magnitude of impedance measured is included in an impedance range of a normal human being, the electronic device 101 may measure the user body information. In contrast, when the magnitude of impedance measured is included in an impedance range of a normal wireless charger, the electronic device 101 may charge the electronic device 101.

As such, when the electronic device 101 includes a coil that may operate as a reception coil, the electronic device 101 may be wirelessly charged with the external magnetic field even without adding a separate hardware component for wireless charging. Thus, no additional process is required for wireless charging, saving processing costs while simplifying the process.

Figure 16:
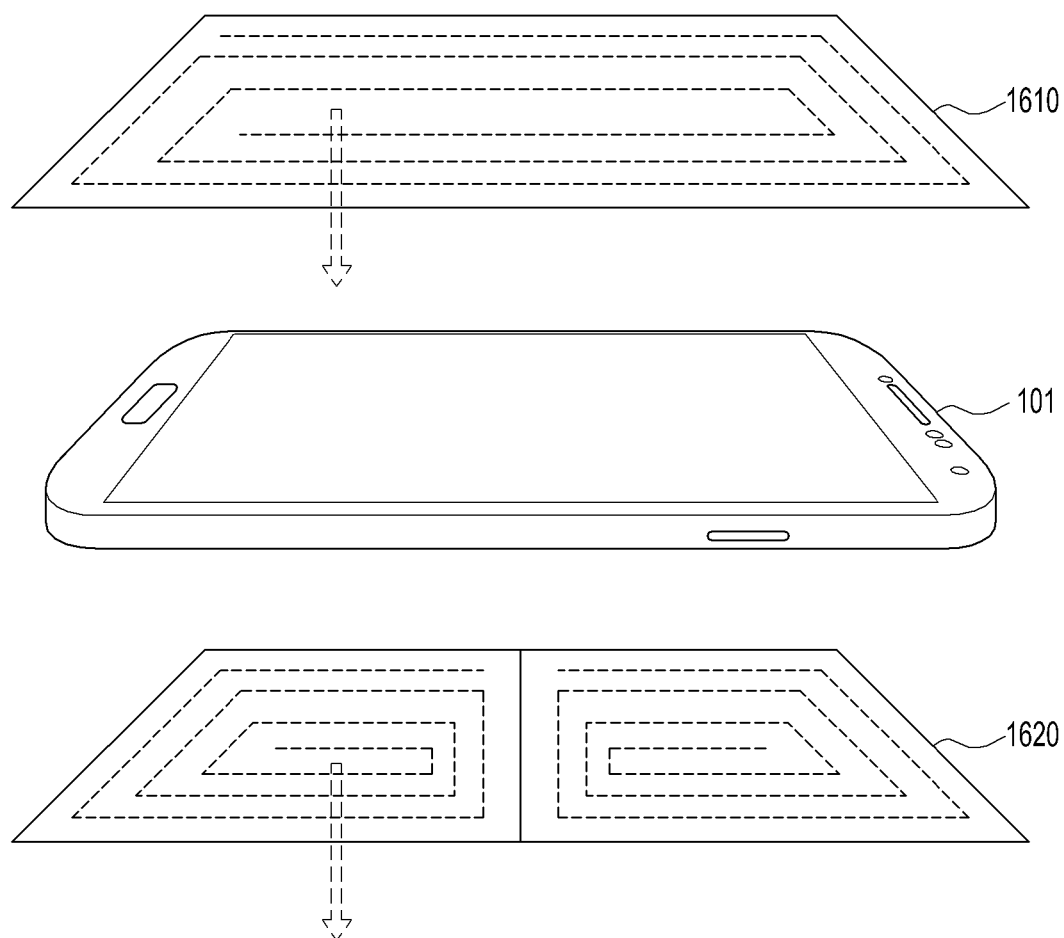
FIG. 16 is a view illustrating a wireless charging method by an electronic device according to an embodiment of the present disclosure.

FIG. 16 is a view illustrating a wireless charging method by an electronic device according to an embodiment of the present disclosure.

Referring to FIG. 16, the wireless charger may include a coil 1610 for generating magnetic field. The wireless charger may apply power to the coil 1610, and when the power is applied to the coil 1610, a magnetic field may be generated by the electromagnetic induction law.

According to an embodiment of the present disclosure, the electronic device 101 may include a transparent film 1620 including at least one of a first coil operated as a source coil and a second coil operated as a reception coil.

When the transparent film 1620 includes the second coil operated as reception coil in the electronic device 101, at least one of a current and voltage may be induced across the second coil by the external magnetic field. The electronic device 101 may perform charging using at least one of the current and voltage induced across the second coil.

As such, the electronic device 101 may use the second coil as an input coil for wireless charging, eliminating the need of adding a hardware component for wireless charger.

Figure 17:
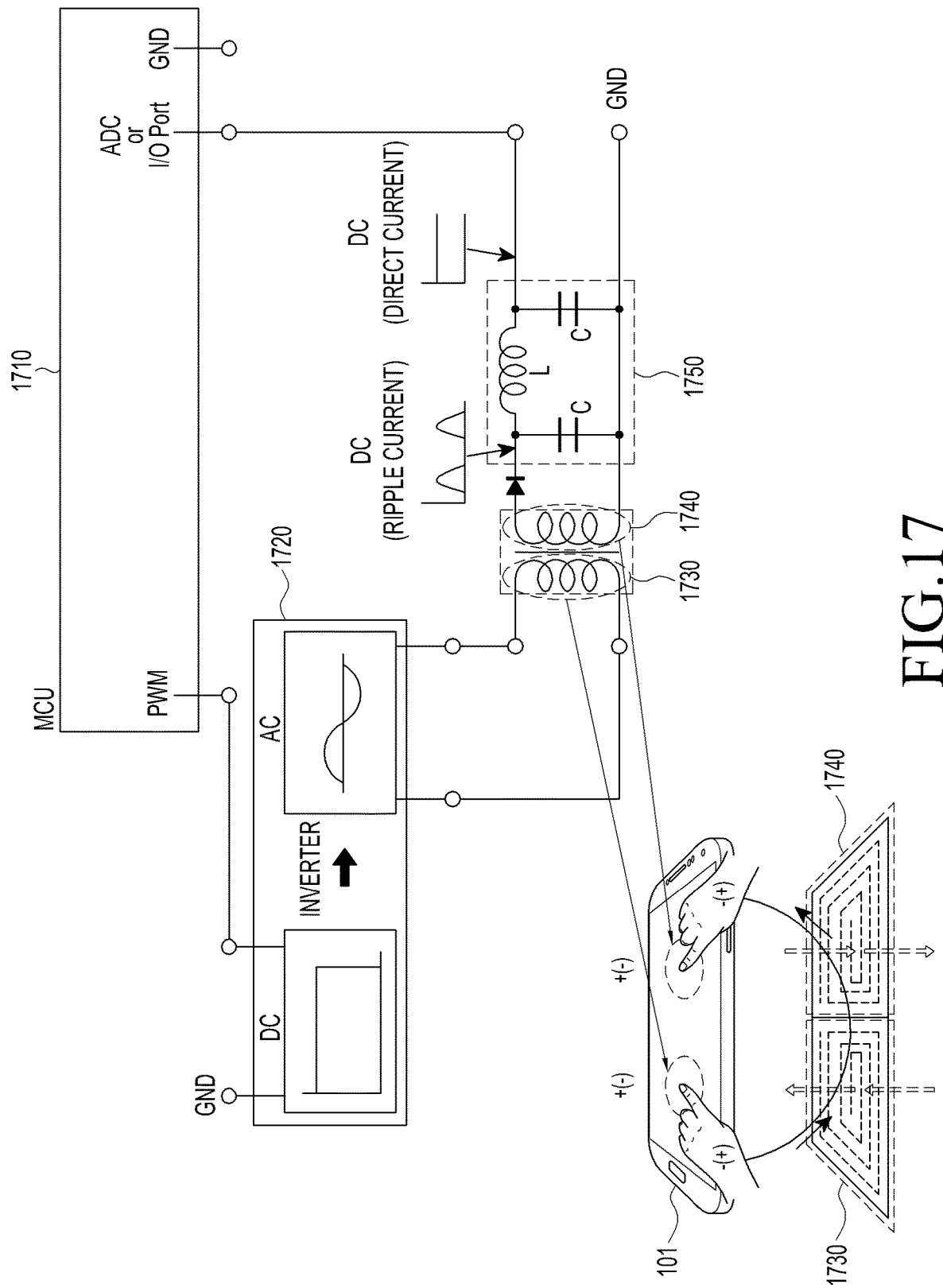
FIG. 17 is a view illustrating a circuit embedded in an electronic device according to an embodiment of the present disclosure.

FIG. 17 is a view illustrating a circuit embedded in an electronic device according to an embodiment of the present disclosure.

Referring to FIG. 17, the electronic device 101 may include a micro control unit (MCU) 1710, a DC-AC converter 1720, a first coil 1730, a second coil 1740, and a rectifying circuit 1750.

Upon identifying contact of the user's body to the touch screen of the electronic device 101, the MCU 1710 may generate a pulse width modulation (PWM) signal and supply the PWM signal to the DC-AC converter 1720. The PWM signal may be generated in such a frequency-adjusted manner that a first magnetic field generated by the first coil may have a predetermined frequency.

The DC-AC converter 1720 may DC-AC convert the received PWM signal and supply the converted AC power to the first coil 1730. The direction of the AC power applied to the first coil may be periodically changed between + and 0. Accordingly, the direction of the first current induced across the user's body by the first magnetic field generated by the first coil 1730 may continuously be changed as well.

The first current may be induced across the user's body by the first magnetic field generated from the first coil 1730, and the second magnetic field may be generated by the first current induced across the user's body. At least one of the second current and voltage may be induced across the second coil 1740 by the second magnetic field. The current and voltage induced across the second coil may be supplied to the rectifying circuit 1750.

The rectifying circuit 1750 may receive the induced second current and voltage and pass only current and voltage with a particular frequency bandwidth through resonance. The current and voltage output through the rectifying circuit 1750 may be input to the ADC or I/O port of the MCU 1710, and the MCU 1710 may measure the current and voltage input to the ADC or I/O port. The MCU 1710 may measure user body information using the measured current and voltage and output the measured user body information.

In an embodiment of the present disclosure, the electronic device 101 may exclude the rectifying circuit 1750. In such case, the second current and voltage induced across the second coil may directly be input to the ADC or I/O port of the MCU 1710. The MCU 1710 may measure the second current and voltage input to the ADC or I/O port. The MCU 1710 may measure user body information using the measured second current and voltage and output the measured user body information.

Figure 18:
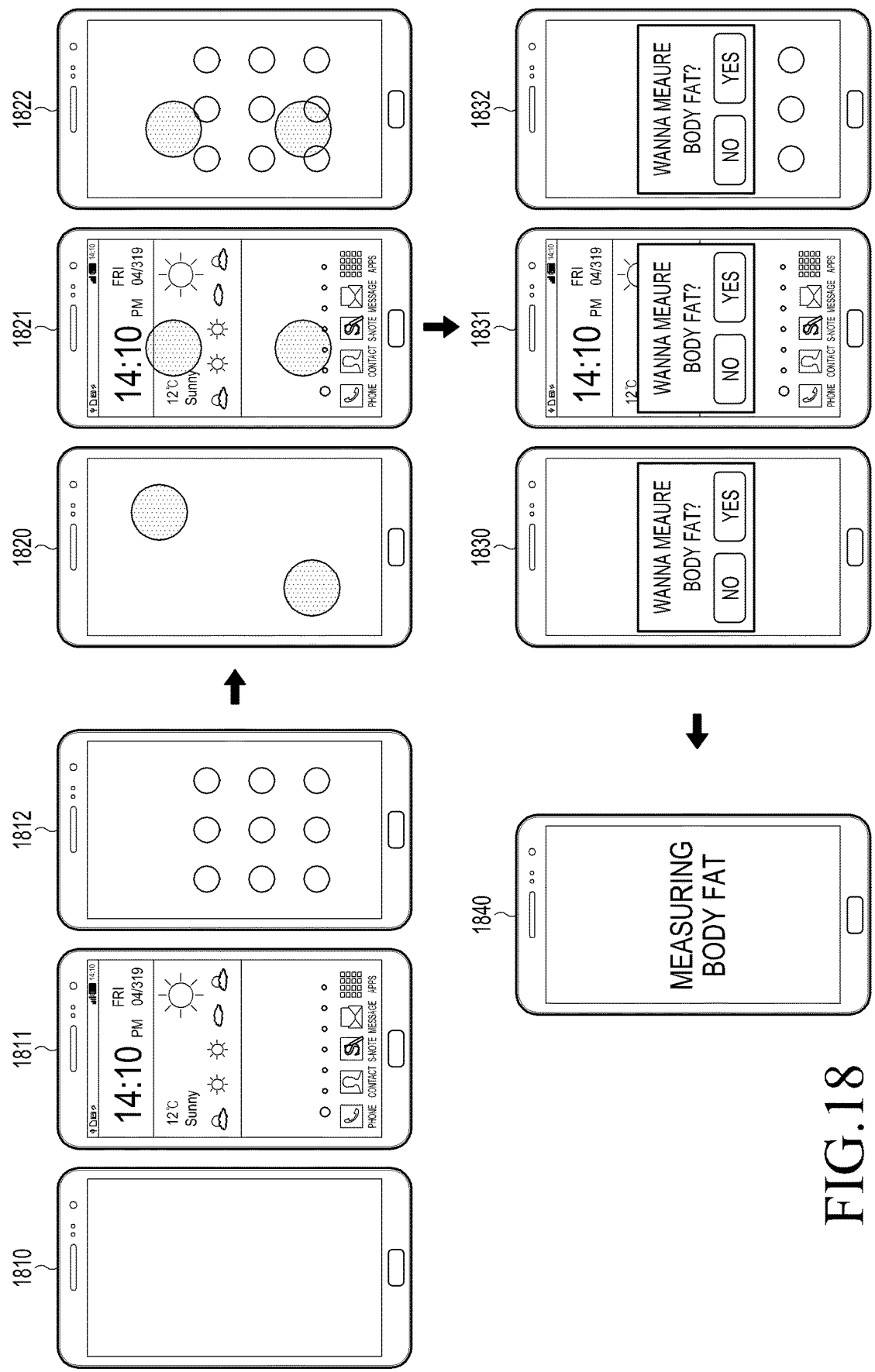
FIG. 18 is a view illustrating an operation for starting to measure body information by an electronic device according to an embodiment of the present disclosure.

FIG. 18 is a view illustrating an operation for starting to measure body information by an electronic device according to an embodiment of the present disclosure.

Hereinafter, the description focuses primarily on body fat information among various types of body information for the purpose of description. However, it is to be understood that this is merely for convenience and conciseness of explanation and not to be construed as limiting application of the present disclosure.

Referring to FIG. 18, the electronic device 101 may display icons corresponding to various applications. The user may select a first icon corresponding to a first application related to measuring body fat among various icons displayed on the electronic device 101 in order to measure his body fat information.

The electronic device 101 may display a menu screen included in the first application after the first application runs. The user may start to measure body fat by the electronic device 101 by selecting a menu item for measuring body fat, such as "measure partial body fat" or "measure whole body fat," in the menu. The user may receive, through the electronic device, information related to managing body fat through a menu item, such as "manage body fat value" or "body fat management tip."

According to an embodiment of the present disclosure, when there is no input from the user, the electronic device 101 may display a standby screen 1810, a home screen 1811, or a pattern input screen 1812.

For example, it is assumed that two portions of the user's body contact the electronic device 101. In this case, the two portions of the user's body may contact the touch screen of the electronic device 101, such as the standby screen 1820, the home screen 1821, or the pattern input screen 1822.

As the two portions of the user's body contact the touch screen, the electronic device 101 may determine whether to start measuring body fat based on at least one of a current and voltage induced across a coil included in the electronic device 101.

When the electronic device 101 determines to start measuring body fat, the electronic device 101 may display a pop-up window for requesting to confirm whether to start the measurement on the standby screen 1830, the home screen 1831, or the pattern input screen 1832. The process of displaying the pop-up window may be omitted by user settings. In other words, the electronic device 101 may perform body fat measurement immediately when determining to start the body fat measurement.

The electronic device 101 may perform body fat measurement when the user confirms to start the body fat measurement through the pop-up window. Further, the electronic device 101 may display a screen 1840 indicating that the body fat measurement is in progress.

FIGS. 19A to 19E are flowcharts illustrating methods for measuring information regarding a user's body based on at least one of a current and voltage induced across a coil included in an electronic device according to an embodiment of the present disclosure.

Figure 19A:
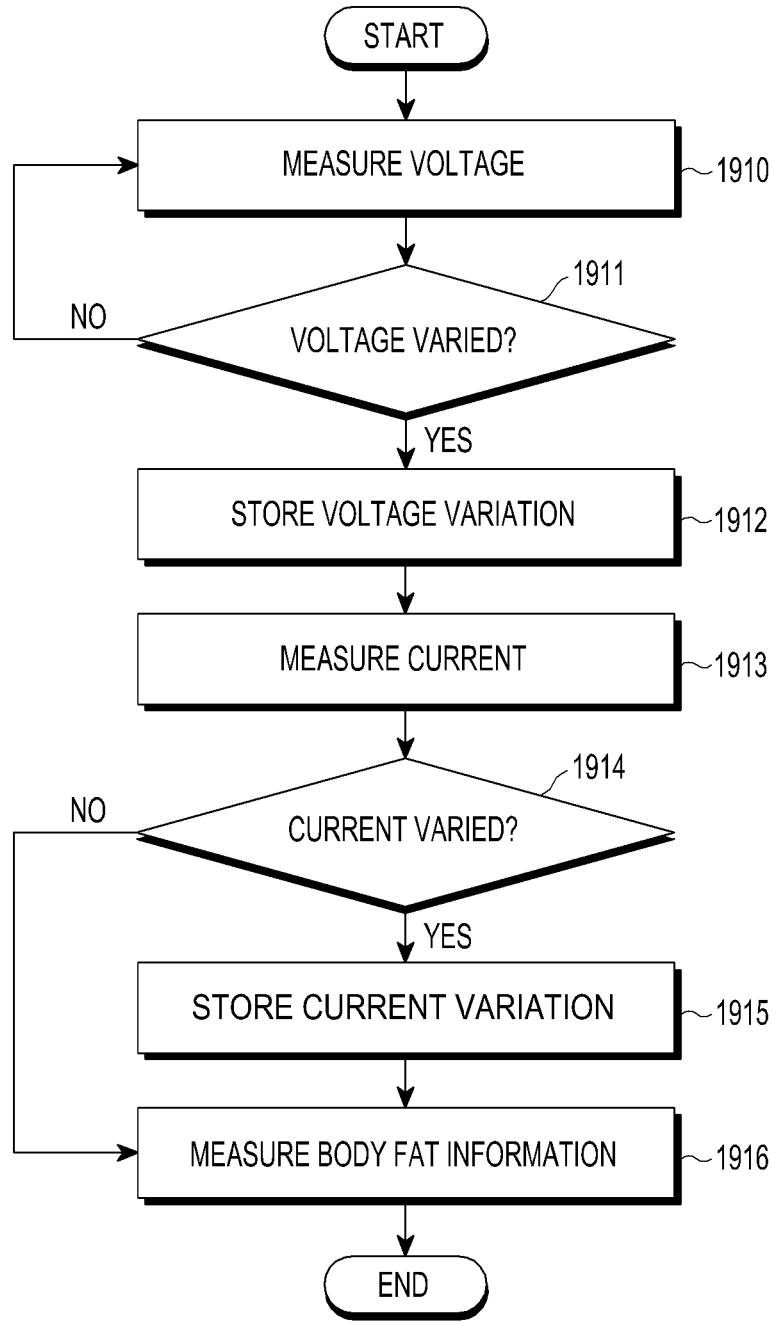
FIGS. 19A to 19E are flowcharts illustrating methods for measuring information regarding a user's body based on at least one of a current and voltage induced across a coil included in an electronic device according to an embodiment of the present disclosure.

FIG. 19A is a flowchart illustrating a method for performing body fat measurement by the electronic device 101 based on whether there is a variation in the current and voltage induced across a coil included in the electronic device 101.

Referring to FIG. 19A, the electronic device 101 may measure the voltage induced across the coil in operation 1910.

In operation 1911, the electronic device 101 may identify whether there is a variation in the voltage induced across the coil. When there is no variation in the voltage, the electronic device 101 may go back to operation 1910 to re-measure voltage induced across the coil.

In operation 1912, when there is a variation in the voltage induced across the coil, the electronic device 101 may store the voltage variation. The electronic device 101 may use the stored voltage variation to measure body fat and to determine whether there is a change in voltage.

In operation 1913, when there is a variation in the voltage induced across the coil, the electronic device 101 may measure the current induced across the coil.

In operation 1914, the electronic device 101 may identify whether there is a variation in the current induced across the coil. Even when there is no variation in the current, the electronic device 101 may measure body fat information using the measured voltage variation alone.

Accordingly, the electronic device 101 may immediately measure body fat information when there is no variation in the current.

In operation 1915, when there is a variation in the current induced across the coil, the electronic device 101 may store the current variation. The electronic device 101 may use the stored current variation to measure body fat and to determine whether there is a change in current.

In operation 1916, the electronic device 101 may measure body fat information.

Although it is illustrated in FIG. 19A that variation in voltage is identified, and variation in current is then identified, variation in current may be identified earlier than variation in voltage. The electronic device 101 may calculate the body fat information only with the current variation, and thus, the electronic device 101 may first identify the current variation. Table 1 shows a relationship between variation in body fat and variation in voltage and current induced across the coil.

TABLE 1

| Variation in body fat | Variation in voltage | Variation in current |
|---|---|---|
| ○ | ○ | ○ |
| ○ | ○ | X |
| ○ | X | ○ |
| X | X | X |

As shown in Table 1 above, the variation in the body fat may be caused based on a variation in at least one of the voltage and current induced across the coil. Accordingly, when at least one of the voltage and current induced across the coil varies, the electronic device 101 may measure the body fat information.

Figure 19B:
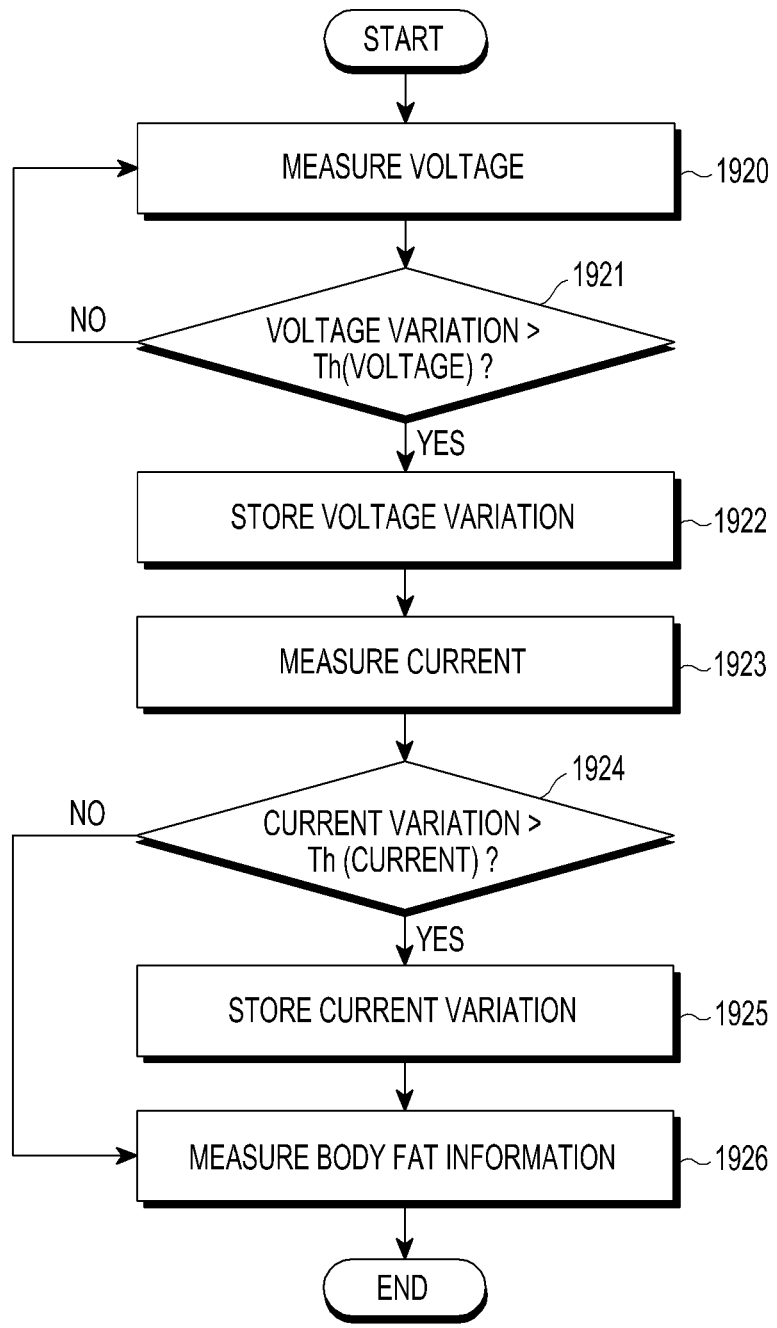

FIG. 19B is a flowchart illustrating a method for performing body fat measurement by the electronic device 101 by comparing a variation in a current and voltage induced across a coil included in the electronic device 101 with a predetermined threshold.

Referring to FIG. 19B, the electronic device 101 may measure the voltage induced across the coil in operation 1920.

In operation 1921, the electronic device 101 may compare the variation in the voltage induced across the coil with a predetermined threshold. When body fat measurement is carried out whenever voltage variations occur, such issue may arise where body fat measurement may be performed even with a tiny voltage variation.

As such, the voltage variation may occur due to, e.g., an error in measuring voltage. Thus, a threshold may be previously set to prevent body fat measurement from being performed when a voltage variation is caused by such voltage measurement error. When the voltage variation is the preset threshold or less, the electronic device 101 may go back to operation 1920 to re-measure voltage induced across the coil.

In operation 1922, the electronic device 101 may store the voltage variation. The stored voltage variation may be used to measure body fat information and to determine whether there is a variation in voltage.

In operation 1923, when the voltage variation exceeds the preset threshold, the electronic device 101 may measure a current induced across the coil.

In operation 1924, the electronic device 101 may compare the variation in the current induced across the coil with a predetermined threshold. As described above in connection with operation 1921, the electronic device 101 may compare the current variation with the present threshold. However, even when the current variation is the preset threshold or less, the electronic device 101 may measure body fat information using only the voltage variation. Accordingly, when the current variation is the preset threshold or less, the electronic device 101 may immediately measure the body fat information.

In operation 1925, when the variation in the current induced across the coil is in excess of the preset threshold, the electronic device 101 may store the current variation. The electronic device 101 may use the stored current variation to measure body fat and to determine whether there is a change in voltage.

In operation 1926, the electronic device 101 may measure body fat information.

Although it is illustrated in FIG. 19B, like FIG. 19A, that variation in voltage is identified, and variation in current is then identified, variation in current may be identified earlier than variation in voltage. Table 2 shows a relationship between variation in body fat and whether the variation in voltage and current induced across the coil exceeds a threshold.

TABLE 2

| Variation in body fat | Voltage variation > Th | Current variation > Th |
|---|---|---|
| ○ | ○ | ○ |
| ○ | ○ | X |
| ○ | X | ○ |
| X | X | X |

As shown in Table 2 above, the variation in the body fat may be caused when at least one of the variations in the voltage and current induced across the coil exceeds the preset threshold.

Accordingly, when at least one of the variations in the voltage and current induced across the coil exceeds the preset threshold, the electronic device 101 may measure the body fat information. In another embodiment of the present disclosure, when at least one of the voltage and current induced across the coil exceeds the preset threshold, the electronic device 101 may also measure the body fat information.

Figure 19C:
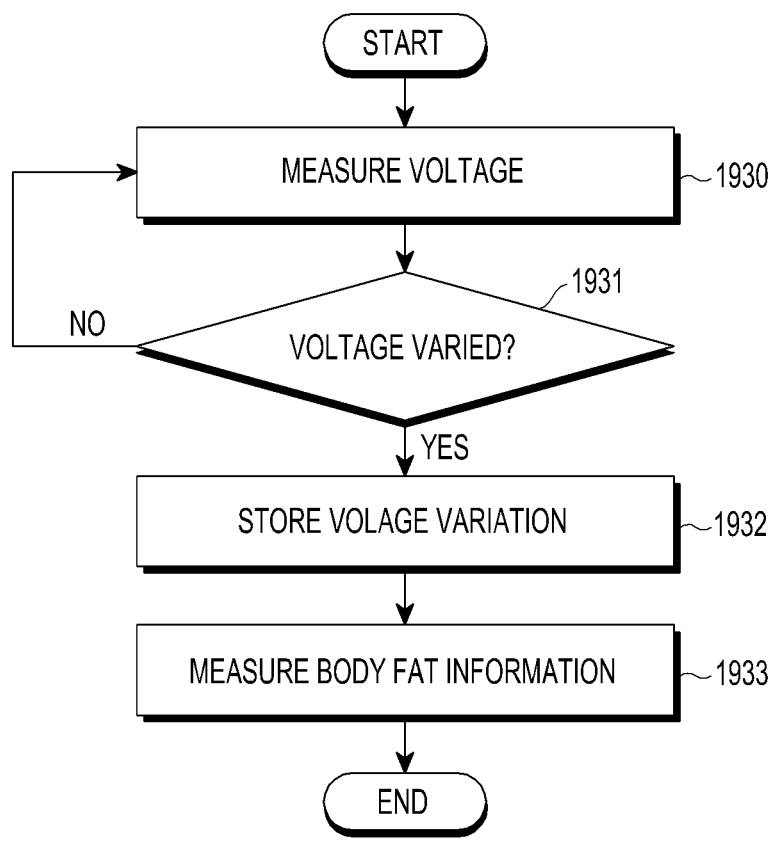

FIG. 19C is a flowchart illustrating a method for performing body fat measurement by the electronic device 101 based on whether there is a change in the voltage induced across a coil included in the electronic device 101.

Referring to FIG. 19C, the electronic device 101 may measure the voltage induced across the coil in operation 1930.

In operation 1931, the electronic device 101 may identify whether there is a variation in the voltage induced across the coil. When there is no variation in the voltage, the electronic device 101 may go back to operation 1930 to re-measure voltage induced across the coil.

In operation 1932, when there is a variation in the voltage induced across the coil, the electronic device 101 may store the variation in the measured voltage. The stored voltage variation may be used to measure body fat information and to determine whether there is a variation in voltage.

In operation 1933, the electronic device 101 may measure body fat information.

As described above in connection with FIG. 19c, the electronic device 101 may measure the body fat information only with the voltage variation. Table 3 shows a relationship between variation in body fat and variation in voltage induced across the coil.

TABLE 3

| Variation in body fat | Variation in voltage | Variation in current |
|---|---|---|
| ○ | ○ | — |
| X | X | — |

As shown in Table 3, the variation in body fat may occur when the voltage induced across the coil is varied. Accordingly, when the voltage induced across the coil varies, the electronic device 101 may measure the body fat information.

Figure 19D:
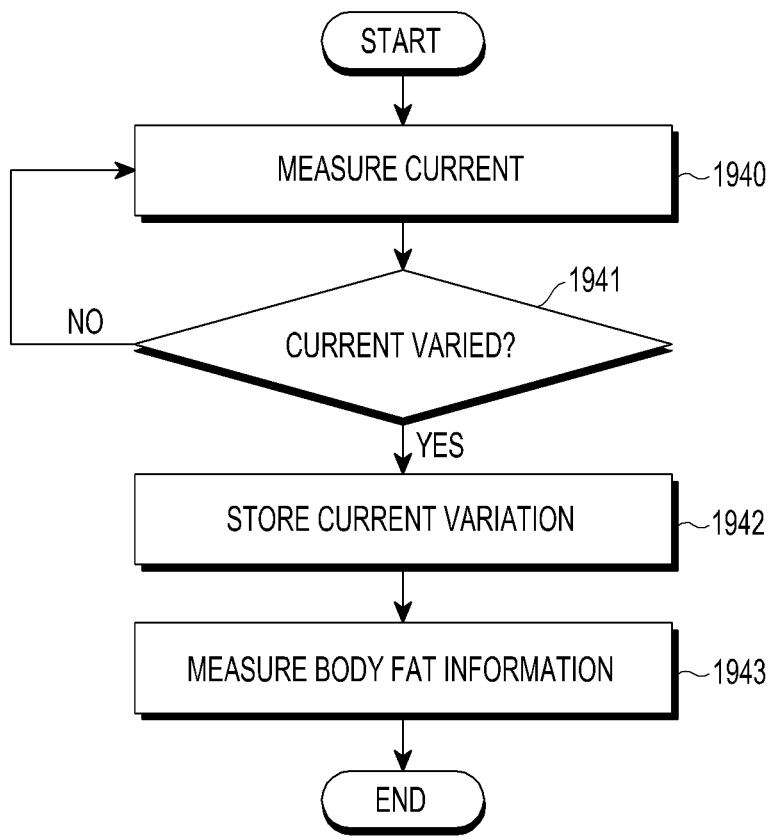

FIG. 19D is a flowchart illustrating a method for performing body fat measurement by the electronic device 101 based on whether there is a change in the current induced across a coil included in the electronic device 101.

Referring to FIG. 19D, the electronic device 101 may measure the current induced across the coil in operation 1940.

In operation 1941, the electronic device 101 may identify whether there is a variation in the current induced across the coil. When there is no variation in the current, the electronic device 101 may go back to operation 1940 to re-measure current induced across the coil.

In operation 1942, when there is a variation in the current induced across the coil, the electronic device 101 may store the variation in the measured current. The stored current variation may be used to measure body fat information and to determine whether there is a variation in current.

In operation 1943, the electronic device 101 may measure body fat information.

Table 4 shows a relationship between variation in body fat and variation in current induced across the coil.

TABLE 4

| Variation in body fat | Variation in voltage | Variation in current |
|---|---|---|
| ○ | — | ○ |
| X | — | X |

As shown in Table 4, the variation in body fat may occur when the current induced across the coil is varied. Accordingly, when the current induced across the coil varies, the electronic device 101 may measure the body fat information.

Figure 19E:
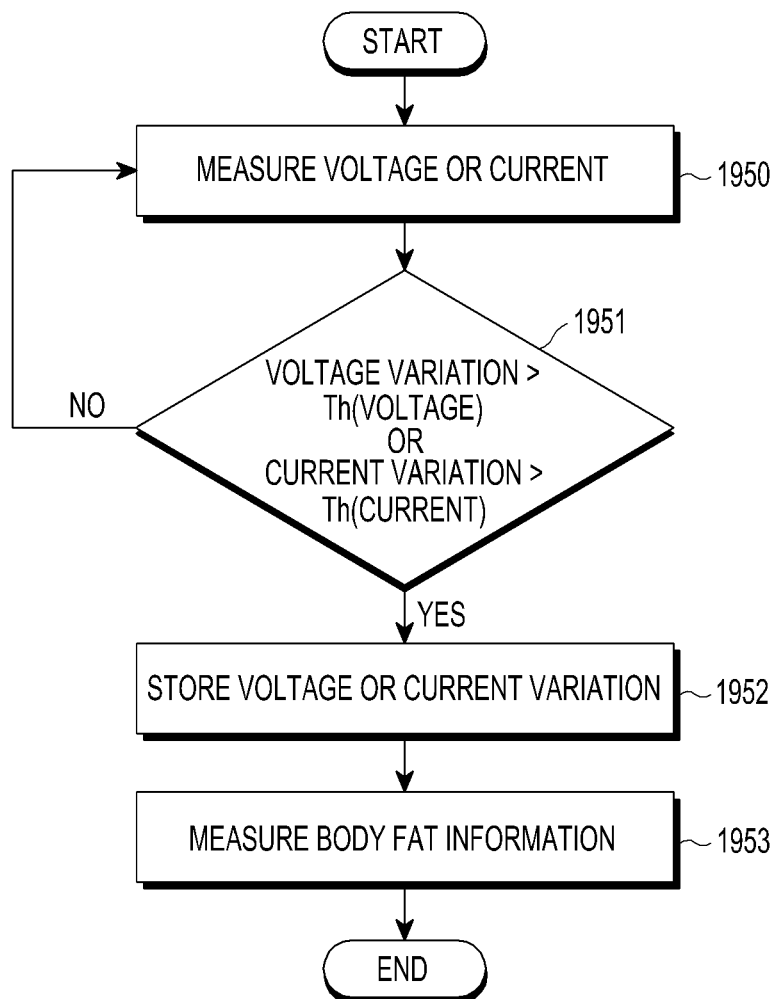

FIG. 19E is a flowchart illustrating a method for performing body fat measurement by the electronic device 101 by comparing a variation in a voltage induced across a coil included in the electronic device 101 with a predetermined threshold.

Referring to FIG. 19E, the electronic device 101 may measure the voltage or current induced across the coil in operation 1950.

In operation 1951, the electronic device 101 may compare the variation in the voltage induced across the coil with a predetermined voltage threshold. The electronic device 101 may compare the variation in the current induced across the coil with a predetermined current threshold. When the voltage variation is the preset voltage threshold or less or the current variation is the preset current threshold or less, the electronic device 101 may go back to operation 1950 to re-measure voltage induced across the coil.

In operation 1952, when the voltage variation exceeds the preset voltage threshold or the current variation exceeds the preset current threshold, the electronic device 101 may store the variation in the measured voltage or current. The stored current variation or voltage variation may be used to measure body fat information and to determine whether there is a variation in current or voltage.

In operation 1953, the electronic device 101 may measure body fat information.

Table 5 shows a relationship between variation in body fat and whether the variation in voltage induced across the coil exceeds a preset threshold.

TABLE 5

| Variation in body fat | Voltage variation > Th | Current variation > Th |
|---|---|---|
| O | O | — |
| X | X | — |

As shown in Table 5 above, the variation in the body fat may be caused when the variation in the voltage induced across the coil exceeds the preset threshold. Accordingly, when the variation in the voltage induced across the coil exceeds the preset threshold, the electronic device 101 may measure the body fat information.

Table 6 shows a relationship between variation in body fat and whether the variation in current induced across the coil exceeds a preset threshold.

TABLE 6

| Variation in body fat | Voltage variation > Th | Current variation > Th |
|---|---|---|
| O | — | O |
| X | — | X |

As shown in Table 6 above, the variation in the body fat may be caused when the variation in the current induced across the coil exceeds the preset threshold. Accordingly, when the variation in the current induced across the coil exceeds the preset threshold, the electronic device 101 may measure the body fat information.

The method for measuring body fat information as described above in connection with FIGS. 19A to 19E may include identifying the area of a contact of the user's body and compensating or adjusting the measured body fat information based on the identified contact area. Accordingly, the electronic device 101 may more precisely provide the body fat information to the user.

Figure 20:
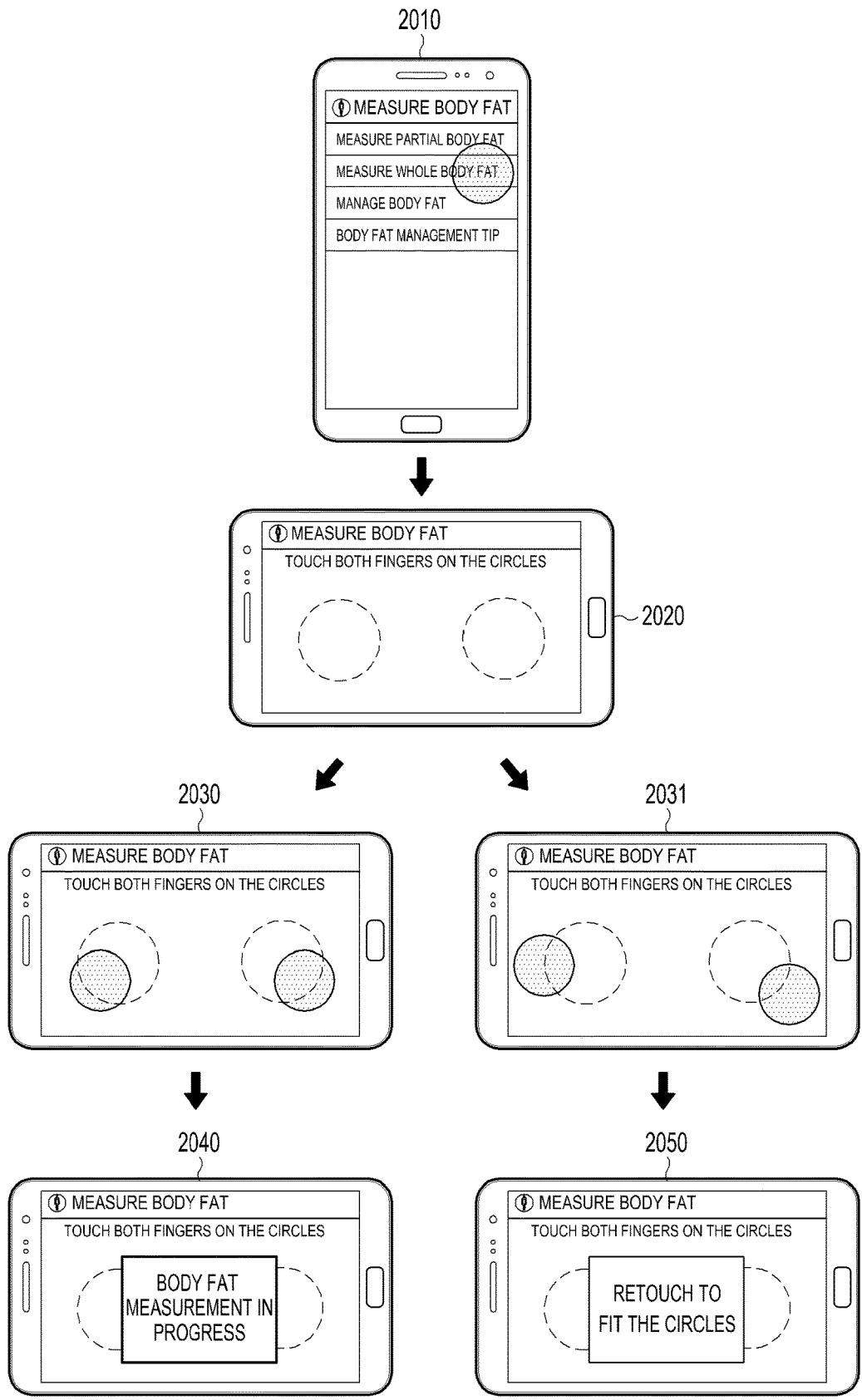
FIG. 20 is a view illustrating an interface output from an electronic device by a full body fat measurement operation according to an embodiment of the present disclosure.

FIG. 20 is a view illustrating an interface output from an electronic device by a full body fat measurement operation according to an embodiment of the present disclosure.

Referring to FIG. 20, the user may select a menu item "measure whole body fat" to measure the whole body fat of the menu screen 2010 displayed on the electronic device 101.

When the user selects the "measure whole body fat" menu item, the electronic device 101 may display a preset area of the touch screen as shown in the screen 2020 in order to measure the whole body fat.

The electronic device 101 may display the area where the contact of the user's body is recognized on the touch screen to overlap the preset area as shown in the screen 2030.

When the contact of the user's body is detected from the preset area through the contact of the user's body as shown in the screen 2030, the electronic device 101 may measure body fat and display the screen 2040 indicating that body fat measurement is in progress.

In contrast, the electronic device 101 may display the area where the contact of the user's body is recognized on the touch screen to overlap the preset area as shown in the screen 2031.

When the contact of the user's body is not identified from the preset area through the contact of the user's body as shown in the screen 2031, the electronic device 101 may display the screen 2050 for inducing the user to contact the preset area again. The electronic device 101 may identify the contact by comparing the preset area with at least one of the area, position, and time of the contact of the user's body on the touch screen.

For example, when the position and area of the contact of the user's body to the preset area departs from the preset area by a predetermined range or more as shown in the screen 2031, the electronic device 101 may fail to detect the contact of the user's body on the preset area.

Figure 21:
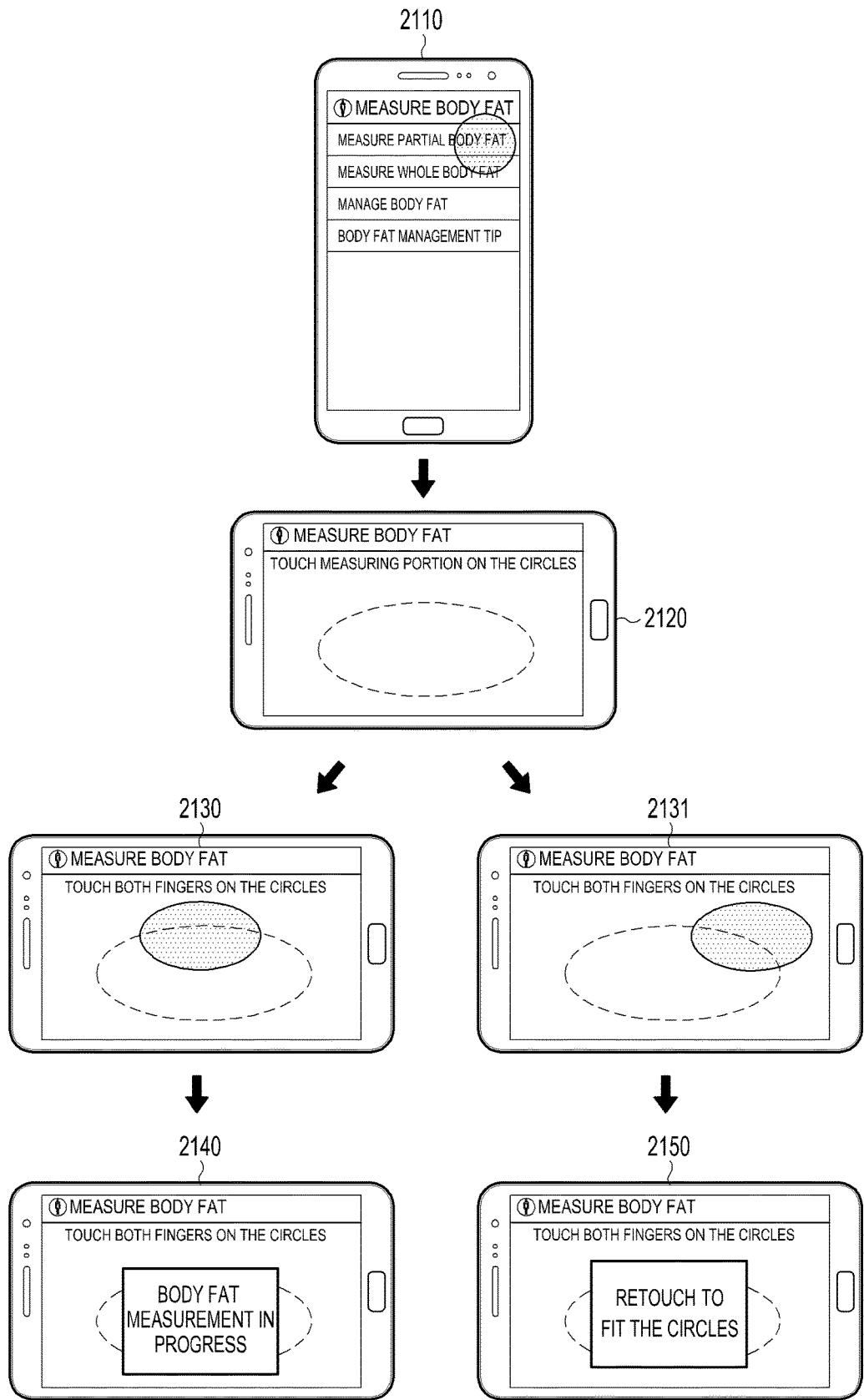
FIG. 21 is a view illustrating a screen of an interface output from an electronic device by a partial body fat measurement operation according to an embodiment of the present disclosure.

FIG. 21 is a view illustrating a screen of an interface output from an electronic device by a partial body fat measurement operation according to an embodiment of the present disclosure.

When measuring partial body fat, unlike measuring the whole body fat, the preset area on the touch screen may be set to be a single larger area. As the preset area is set to be larger, the area of the contact between the user's body and the touch screen may increase. Accordingly, although the preset area is set to be a single area, the electronic device 101 may recognize as if the user's body contacts at least two spots on the touch screen.

Referring to FIG. 21, the user may select a menu item "measure partial body fat" to measure the whole body fat of the menu screen 2110 displayed on the electronic device 101.

When the user selects the "measure partial body fat" menu item, the electronic device 101 may display a preset area of the touch screen as shown in the screen 2120 in order to measure the whole body fat.

The electronic device 101 may display the area where the contact of the user's body is recognized on the touch screen to overlap the preset area as shown in the screen 2130.

When the contact of the user's body is identified from the preset area through the contact of the user's body as shown in the screen 2130, the electronic device 101 may measure body fat and display the screen 2140 indicating that body fat measurement is in progress.

In contrast, the electronic device 101 may display the area where the contact of the user's body is recognized on the touch screen to overlap the preset area as shown in the screen 2131.

When the contact of the user's body is not identified from the preset area through the contact of the user's body as shown in the screen 2131, the electronic device 101 may display the screen 2150 for inducing the user to contact the preset area again. The electronic device 101 may identify the contact by comparing the preset area with at least one of the area, position, and time of the contact of the user's body on the touch screen.

For example, when the position and area of the contact of the user's body to the preset area departs from the preset area by a predetermined range or more as shown in the screen 2131, the electronic device 101 may fail to detect the contact of the user's body on the preset area.

Figure 22:
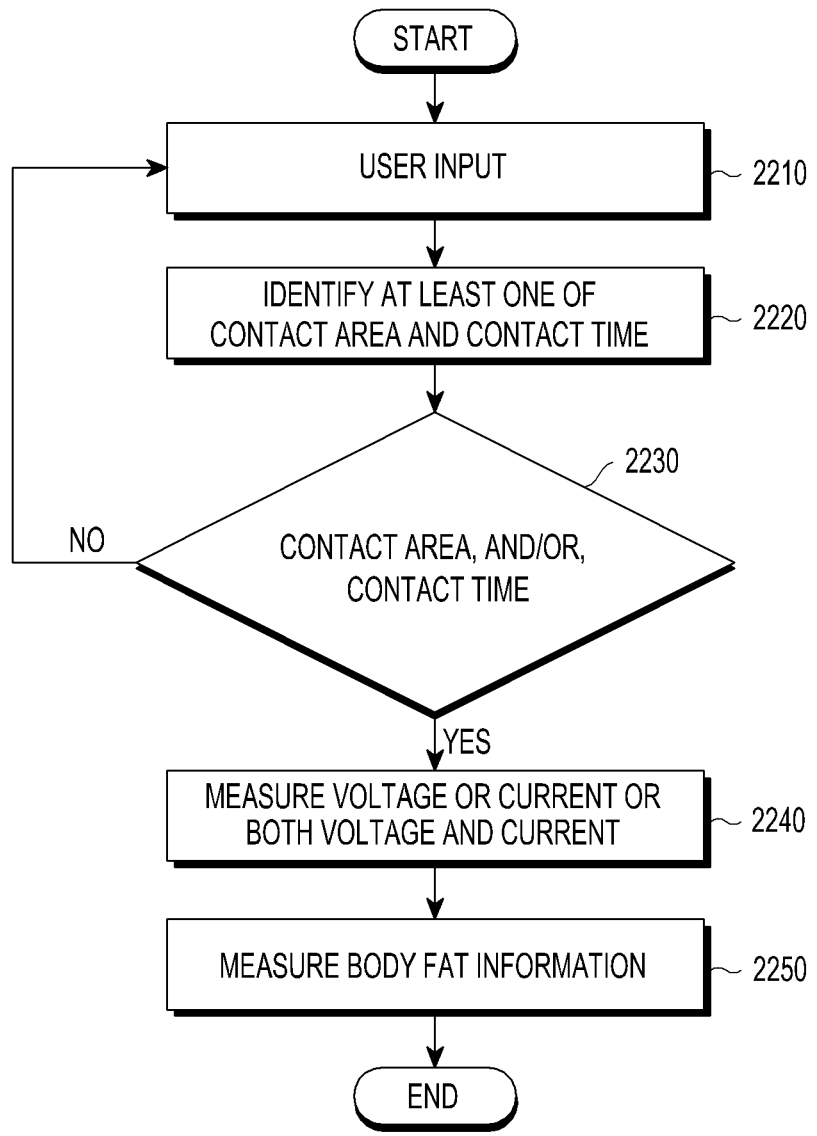
FIG. 22 is a flowchart illustrating a method for measuring body information by detecting a contact with a user's body by an electronic device according to an embodiment of the present disclosure.

FIG. 22 is a flowchart illustrating a method for measuring body information by detecting a contact with a user's body by an electronic device according to an embodiment of the present disclosure.

Described in connection with FIG. 22 is a method for detecting a contact of the user's body using at least one of the area and time of the contact of the user's body.

Referring to FIG. 22, the electronic device 101 may obtain a user input for measuring body fat information in operation 2210. The user input may be obtained as the user's body contacts the touch screen.

In operation 2220, the electronic device 101 may identify at least one of the contact area and contact time of the user's body.

In operation 2230, the electronic device 101 may compare the identified contact area with a preset threshold contact area. Further, the electronic device 101 may compare the identified contact time with a preset threshold contact time.

Further, the electronic device 101 may compare the identified contact area and contact time with the threshold contact area and the threshold contact time, respectively.

When the identified contact area is the preset threshold contact area or less or when the identified contact time is the preset threshold contact time or less, the electronic device 101 may display a message to induce the user to touch again his body to the touch screen.

In operation 2240, when the identified contact area exceeds the preset threshold contact area or the identified contact time exceeds the preset threshold contact time, the electronic device 101 may measure at least one of the current and voltage induced across a coil embedded in the electronic device 101. Further, according to user settings, the electronic device 101, when both the contact area and the contact time exceed the preset thresholds, may measure at least one of the current and voltage induced across the coil.

In operation 2250, the electronic device 101 may measure body fat information using at least one of the measured current and voltage.

Table 7 shows a relationship between whether the electronic device 101 identifies contact and whether the identified contact area exceeds the preset threshold contact area and whether the identified contact time exceeds the preset threshold contact time.

TABLE 7

| Contact identified | Contact area > Th | Contact time > Th |
|---|---|---|
| ○ | ○ | ○ |
| X | ○ | X |
| X | X | ○ |
| X | X | X |

As shown in Table 7, when the contact area of the user's body exceeds the preset threshold contact area and the contact time exceeds the preset threshold contact time, the electronic device 101 may identify the contact and start to measure body fat. For example, when the contact area exceeds 1 cm$^2$ and the contact time lasts two seconds or more under the situation where the user's body contact occurs, the electronic device 101 may identify as a body contact and start to measure body fat.

Figure 23A:
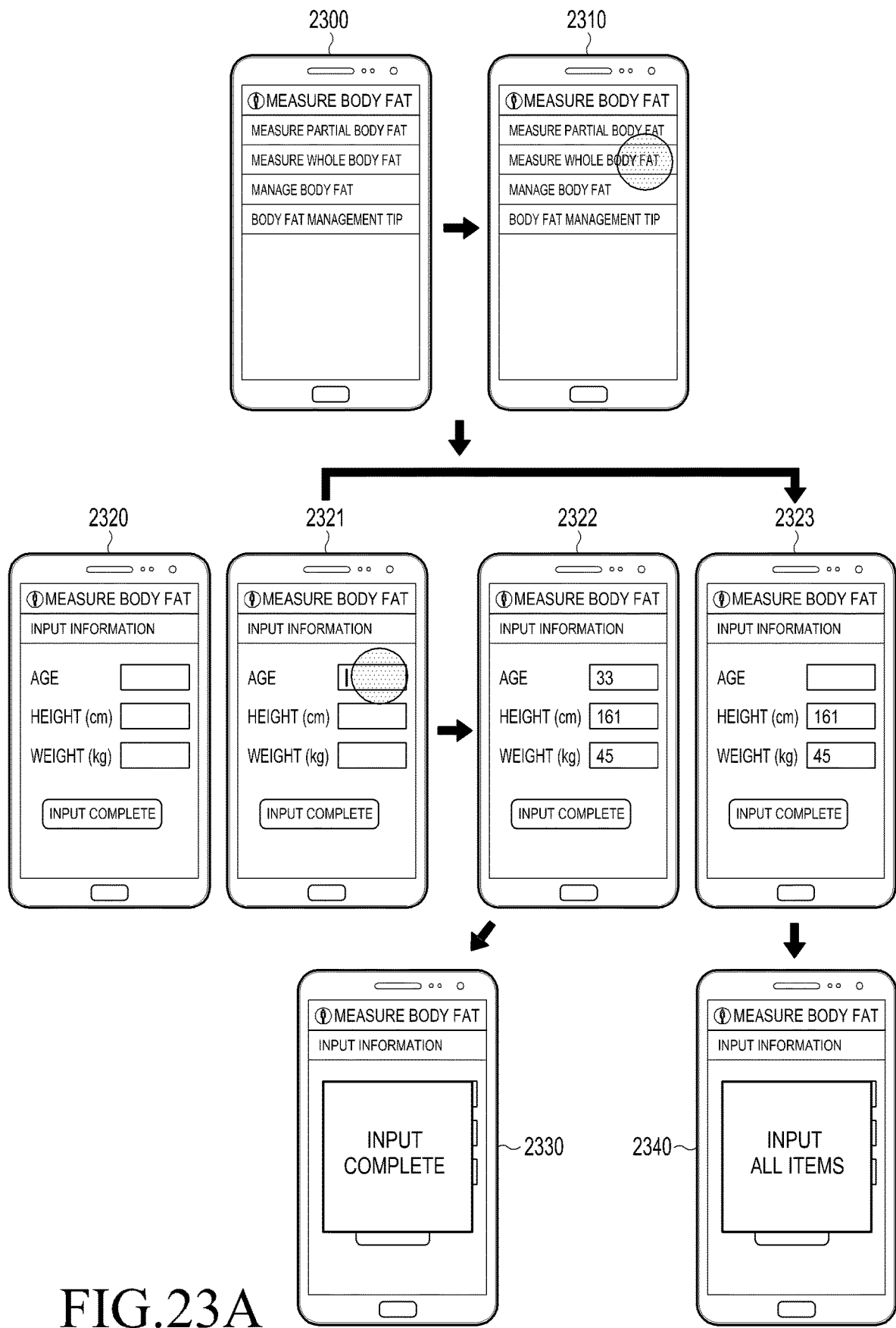
FIGS. 23A and 23B are views illustrating screens of an interface output from an electronic device by an operation of inputting body information according to an embodiment of the present disclosure.
Figure 23B:
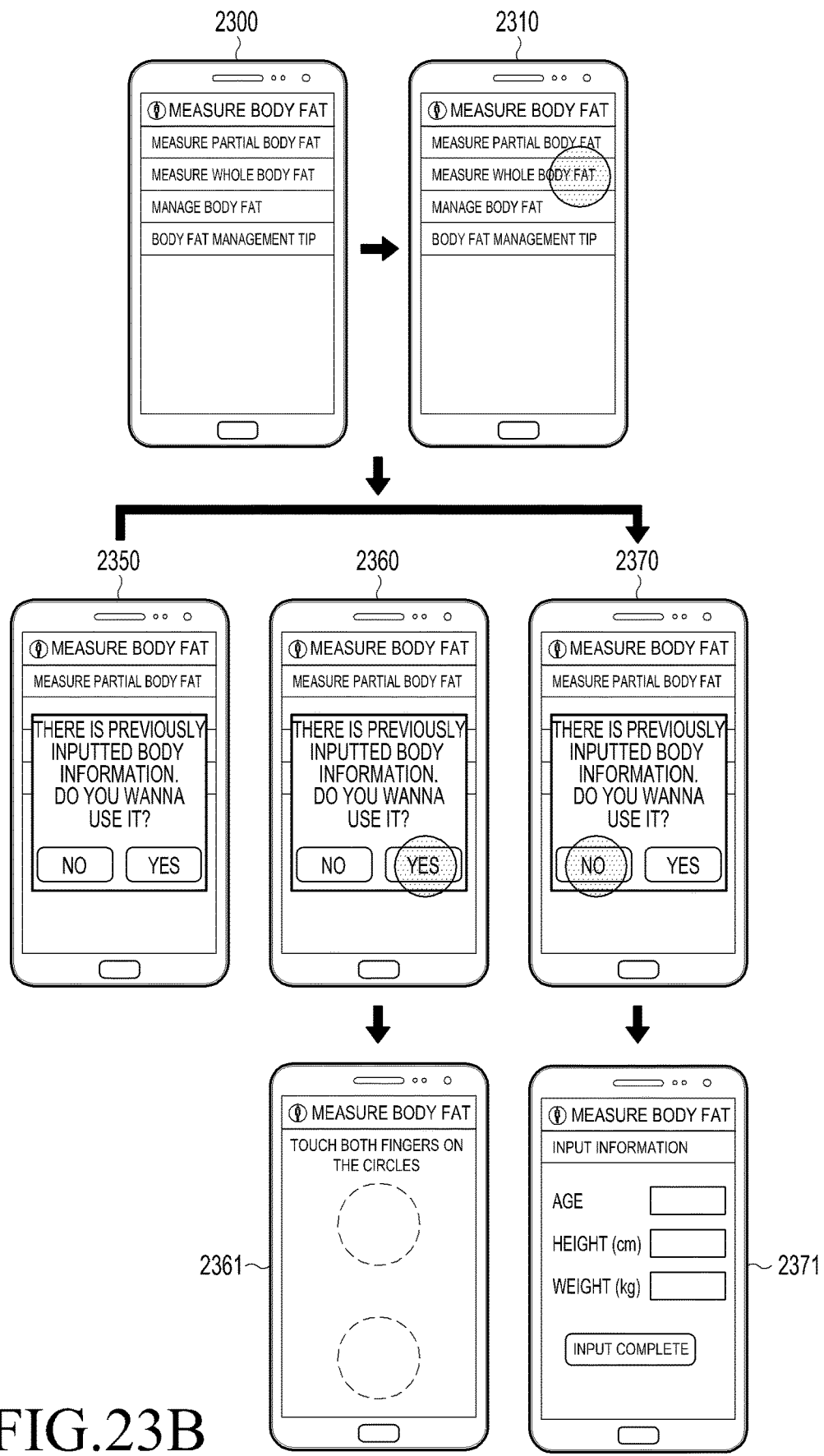

FIGS. 23A and 23B are views illustrating screens of an interface output from an electronic device by an operation of inputting body information according to an embodiment of the present disclosure.

Referring to FIG. 23A, a method for inputting user body information to measure body fat is described.

The electronic device 101, when an application for measuring body fat runs, may display a menu screen 2300 included in the application. The user may select a menu item "measure whole body fat" or "measure partial body fat" to measure the whole body fat of the menu screen 2310 displayed on the electronic device 101.

When the user selects the menu item "measure whole body fat" or "measure partial body fat," the electronic device 101 may display a user body information input screen 2320 for measuring body fat.

The user may select each type of user body information and input his body information. For example, the user may input his age on the screen 2321 displaying body information items.

When the user inputs all body information items, the user may select an "input complete" box displayed on a lower portion of the body information input screen 2322.

When the user inputs all body information items, the electronic device 101 may display a screen 2330 indicating that the body information input has been complete.

Further, when the user does not input all body information items, the user may also select an "input complete" box displayed on a lower portion of the body information input screen 2323.

When the user does not input all body information items, the electronic device 101 may display a screen 2340 requesting to input body information.

A method for using user body information previously inputted is described with reference to FIG. 23A.

The electronic device 101, when an application for measuring body fat runs, may display a menu screen 2300 included in the application. The user may select a menu item "measure whole body fat" or "measure partial body fat" to measure the whole body fat of the menu screen 2310 displayed on the electronic device 101.

When the user selects the menu item "measure whole body fat" or "measure partial body fat" and there is body information previously inputted, the electronic device 101 may display, on the screen 2350, a pop-up window for identifying whether to use the previously inputted body information.

The user may select whether to use the previously inputted body information through the pop-up window displayed on the screens 2360 and 2370.

When the user selects to use the previously inputted body information, the electronic device 101 may display a preset area for measuring body fat on the screen 2361. In contrast, when the user selects not to use the previously inputted body information, the electronic device 101 may display the user body information input screen 2371 for measuring body fat.

Figure 24A:
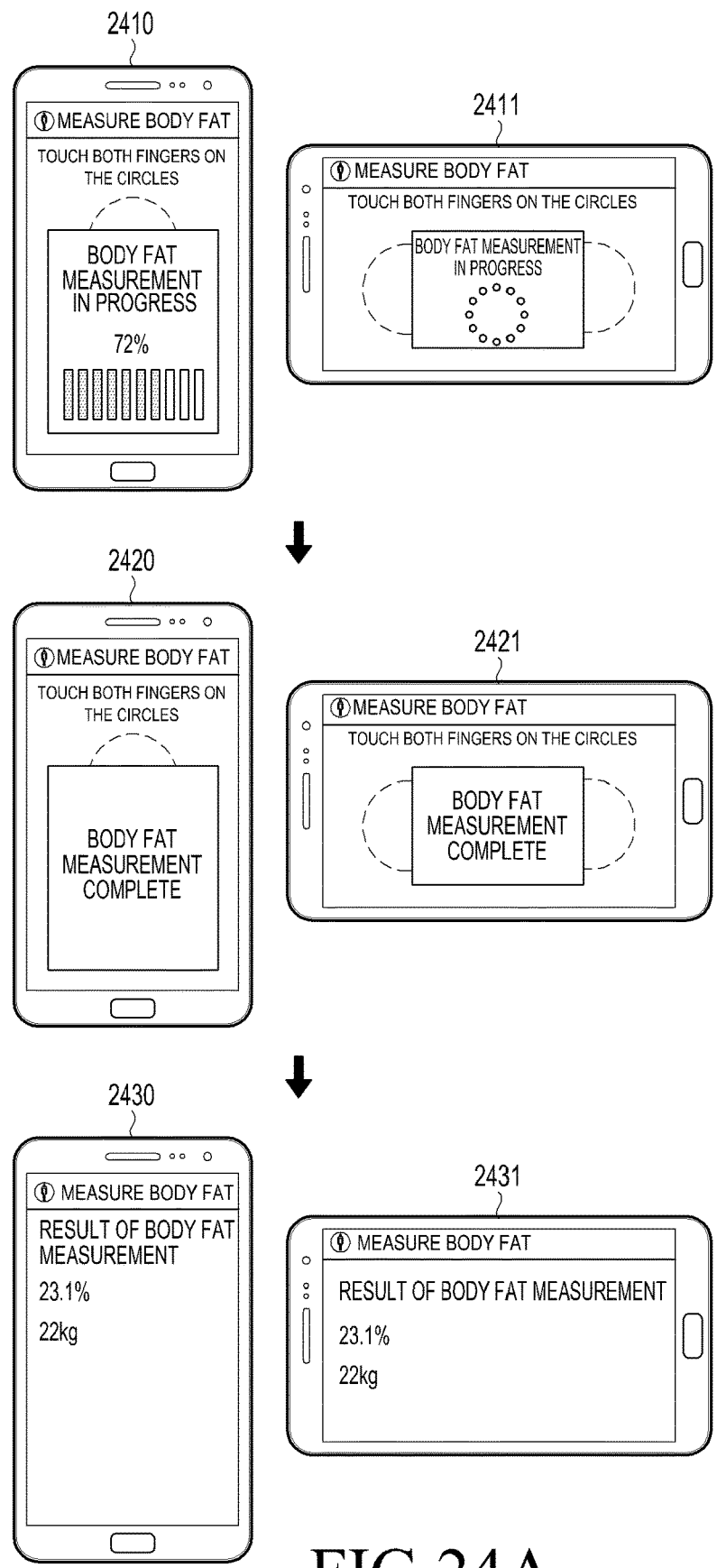
FIGS. 24A and 24B are views illustrating various screens of an interface showing user body information measured according to an embodiment of the present disclosure.
Figure 24B:
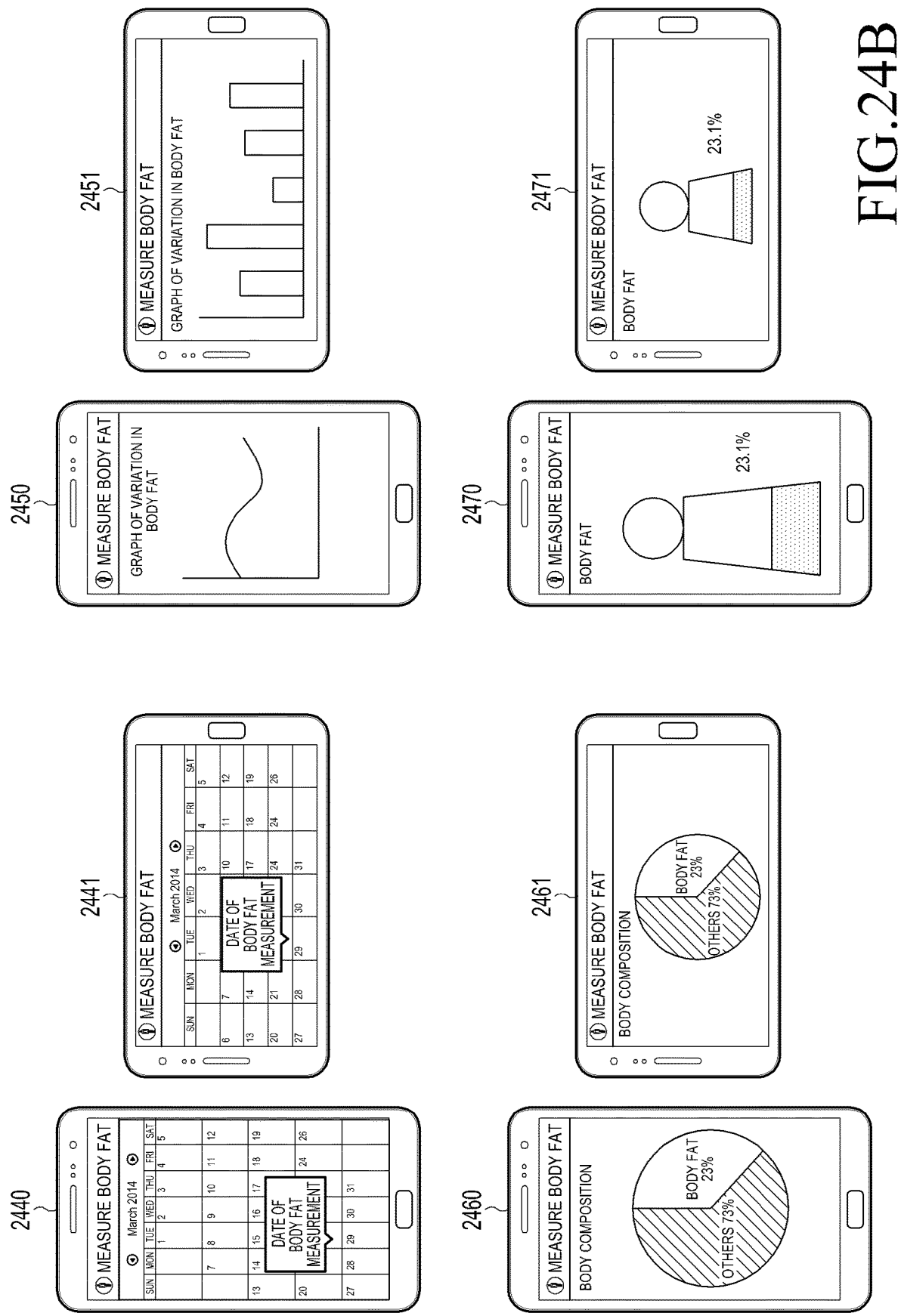

FIGS. 24A and 24B are views illustrating various screens of an interface showing user body information measured according to an embodiment of the present disclosure.

Referring to FIG. 24A, a method for displaying a result of measuring body fat is described.

The electronic device 101, upon identifying that the user's body contacts, may measure body fat. The electronic device 101 may display the progress of the body fat measurement on the screen 2410 and 2411.

The electronic device 101, upon completing the body fat measurement, may display screens 2420 and 2421 to indicate that the measurement is complete. Thereafter, the electronic device 101 may display the result of body fat measurement on the screens 2430 and 2431.

FIG. 24B shows various UIs displaying the result of body fat measurement by the electronic device 101.

Referring to FIG. 24B, the electronic device 101 may display the result of body fat measurement on the screens 2440 and 2441 where a calendar is displayed. For example, the result of body fat measurement may be displayed on the date when the user measured the body fat information.

The electronic device 101 may display graphs of variations in body fat on the screens 2450 and 2451 using the stored result of body fat information measurement. Accordingly, the user may identify the trend of the variation in body fat.

The electronic device 101 may display pie graphs indicating the body composition of the user's body on the screens 2460 and 2461 using the measured body fat information and may display the body composition on the screens 2470 and 2471 using a human-like image.

Figure 25:
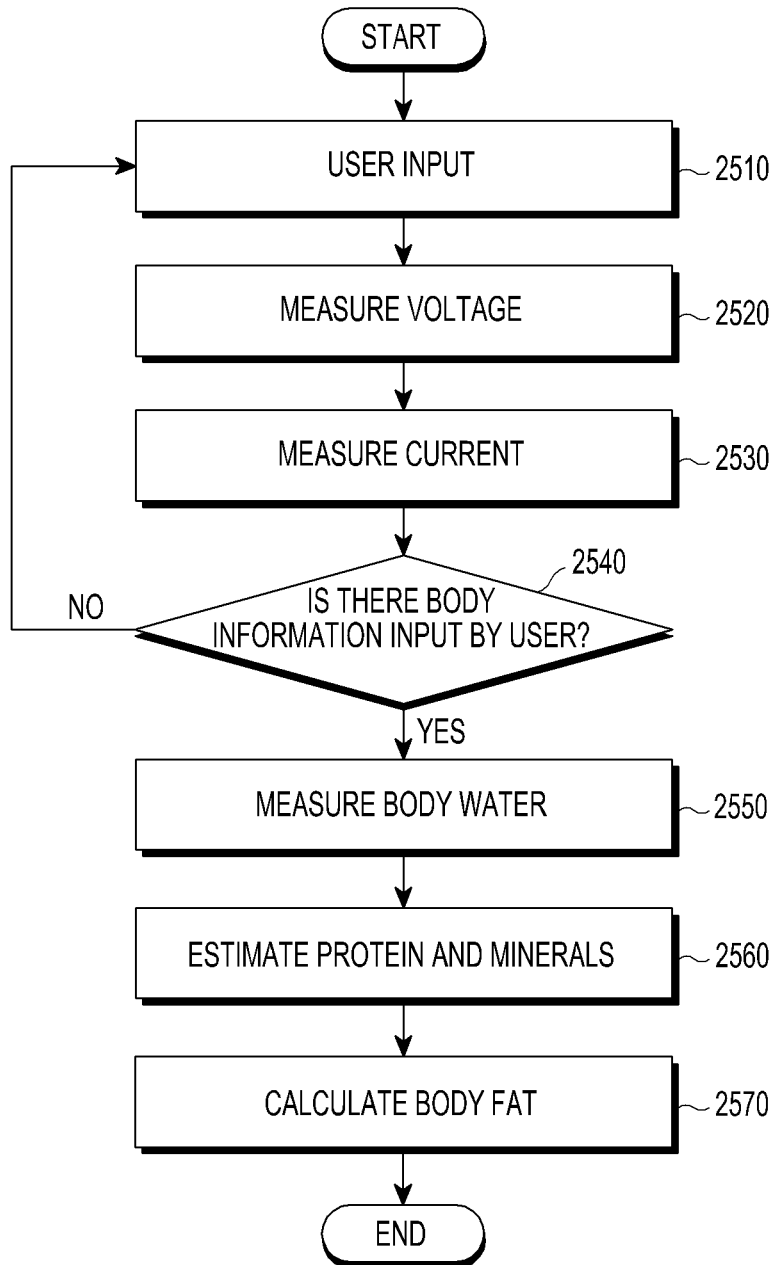
FIG. 25 is a flowchart illustrating a method for calculating body fat by an electronic device according to an embodiment of the present disclosure.

FIG. 25 is a flowchart illustrating a method for calculating body fat by an electronic device according to an embodiment of the present disclosure.

Referring to FIG. 25, a method for calculating the user's body fat by measuring or estimating a current and voltage induced across the electronic device 101 by the electronic device 101 is described.

In operation 2510, the electronic device 101 may obtain a user input indicating body information for measuring body fat information. The user, after inputting the body information, may measure body fat by touching his body to the touch screen.

In operation 2520, the electronic device 101 may measure the voltage induced across a coil included in the electronic device 101.

In operation 2530, the electronic device 101 may measure the current induced across a coil included in the electronic device 101. Both operation 2520 and operation 2530 may not be performed, or only one of operation 2520 and operation 2530 may be performed. The current may be estimated by the measured voltage, and the voltage may be estimated by the measured current.

In operation 2540, the electronic device 101 may determine whether there is the user's body information. When there is no user body information as inputted by the user, such as height or weight, the electronic device 101 may go back to operation 2510 to induce the user to input the body information. When the body information as inputted by the user, such as height or weight, is absent, previously inputted body information may be used to measure body fat.

In operation 2550, the electronic device 101 may measure body water in the user's body when the user's height, among other body information, is present. The user's body water may be measured by an electrical method. For example, when an electric current is rendered to flow across the user's body, the current flows along high conductive materials or substances (body water). The more body water the user has, the better the current flows. By such principle, the body resistance, i.e., the body impedance, may be measured. The impedance is a force against the flow of electric current and may be represented as in Equation 1 in the form of the sum of electric resistance and reactance.

$$Z = R + iX \qquad \text{Equation 1}$$

Here, i is an imaginary number. The user's body water may be calculated using the measured impedance. The body water may be obtained by multiplying value obtained by dividing the square of the user's height by the human resistance (impedance) by a preset constant as shown in Equation 2.

$$\text{body water} = \frac{H^2}{Z} \times K \qquad \text{Equation 2}$$

Here, H is the user's height, and K is the preset constant for measuring body water. As such, the electronic device 101 may measure the user's body water using the user's height and the measured impedance.

In operation 2560, the electronic device 101 may estimate the protein and minerals for the user's body. The electronic device 101 may estimate the protein and minerals as per a proportional relation using the measured body water. The proportional relation may be previously set according to the relation between the body water, the amount of protein, and the amount of minerals.

In operation 2570, the electronic device 101 may calculate the body fat of the user's body. The electronic device 101 may calculate the body fat amount by deducting the body water, the amount of protein, and the amount of minerals from the user's weight. The user's weight may be obtained in the process of inputting the user body information in operation 2510. The method of calculating body fat described above in connection with FIG. 25 is merely an example, and the present disclosure is not limited thereto. Other methods may be adopted to calculate the body fat information using the voltage or current measured, and body fat estimation may be performed instead of body fat measurement.

Figure 26:
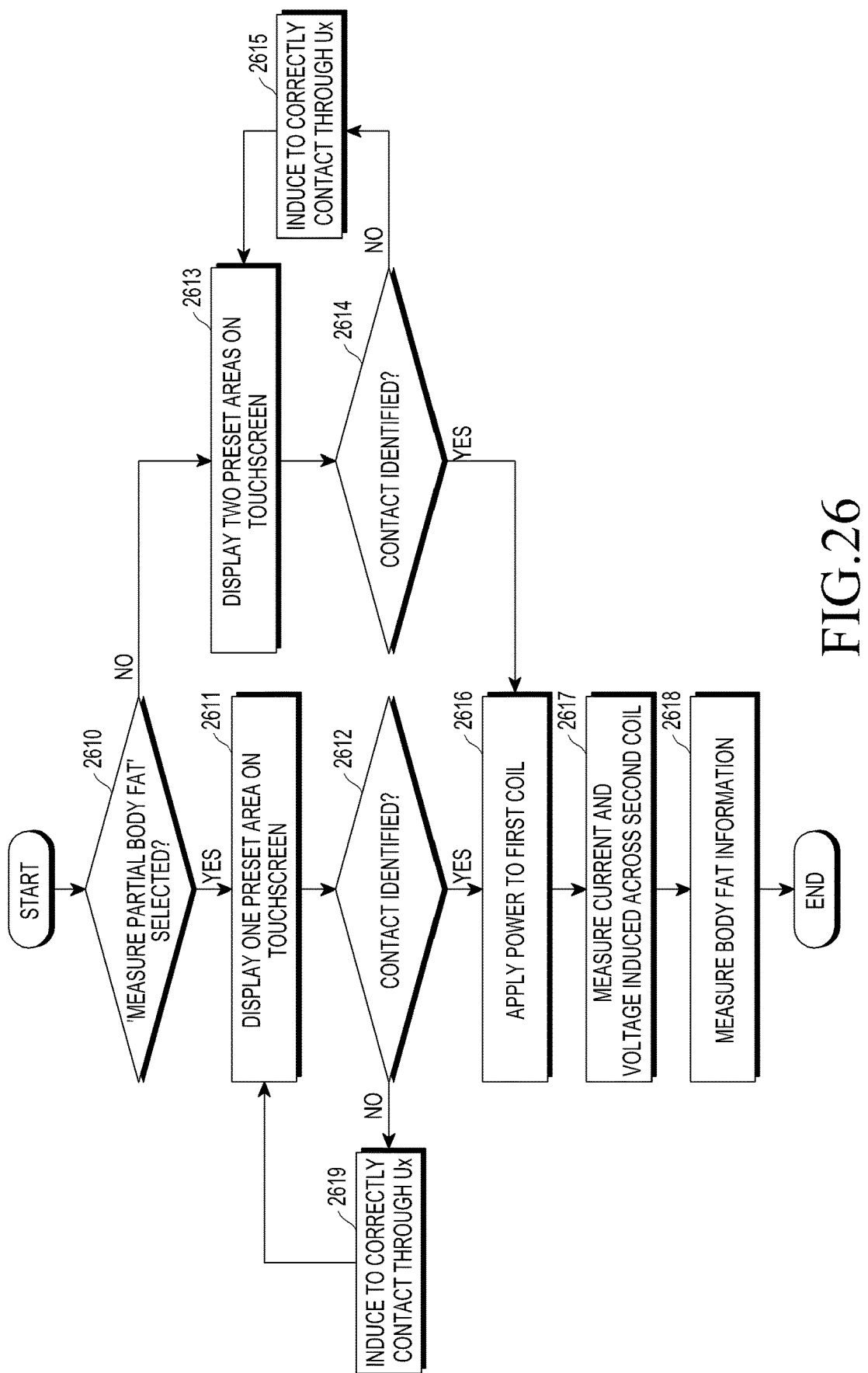
FIG. 26 is a flowchart illustrating a method for measuring body fat by an electronic device according to an embodiment of the present disclosure.

FIG. 26 is a flowchart illustrating a method for measuring body fat by an electronic device according to an embodiment of the present disclosure.

Referring to FIG. 26, the electronic device 101 may identify whether the user selects to measure partial body fat in operation 2610. Depending on whether to measure partial body fat or whole body fat, the preset area for measuring body fat by the electronic device 101 may be varied. Accordingly, the electronic device 101 may determine which one of measuring partial body fat and measuring whole body fat has been selected by the user through a body fat measurement application.

In operation 2611, the electronic device 101, when the user selects to measure partial body fat, may display a preset area on the touch screen of the electronic device 101. Since partial body fat is measured using only current flowing across one area, the electronic device 101 may display only the single preset area.

In operation 2612, the electronic device 101 may identify a contact of the user's body on at least one preset area. In operation 2619, upon failure to identify the contact, the electronic device 101 may induce the user to make a right contact through the UX.

In operation 2613, the electronic device 101, when the user selects not to measure partial body fat but to measure whole body fat, may display two preset areas on the touch screen of the electronic device 101. Since the whole body fat is measured using the current flowing across the user's body through the two areas, the electronic device 101 may display only the two preset areas.

In operation 2614, the electronic device 101 may identify a contact of the user's body on at least two preset areas. In operation 2615, upon failure to identify the contact, the electronic device 101 may induce the user to make a right contact through the UX.

In operation 2616, the electronic device 101 may apply power to the first coil included in the electronic device 101 to measure body fat.

In operation 2617, the electronic device 101 may measure the current and voltage induced across the second coil included in the electronic device 101.

In operation 2618, the electronic device 101 may measure the user's partial body fat or whole body fat using the current and voltage induced across the second coil.

Figure 27:
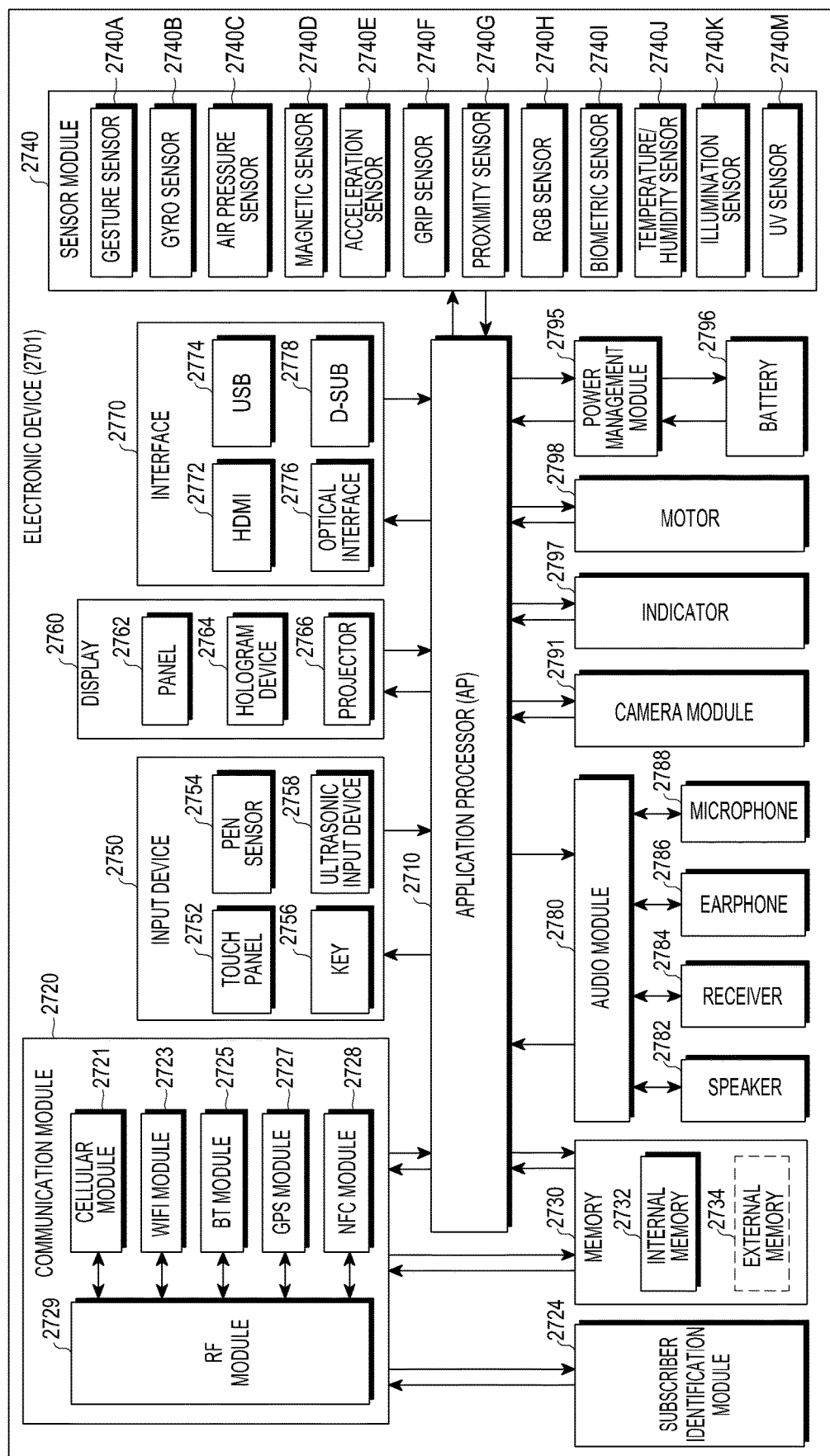
FIG. 27 is a block diagram illustrating an electronic device according to an embodiment of the present disclosure.

FIG. 27 is a block diagram illustrating an electronic device according to an embodiment of the present disclosure.

Referring to FIG. 27, the electronic device 2701 may include the whole or part of the configuration of, e.g., the electronic device 101 shown in FIG. 1. The electronic device 2701 may include one or more processors (e.g., APs) 2710, a communication module 2720, a subscriber identification module (SIM) 2724, a memory 2730, a sensor module 2740, an input device 2750, a display 2760, an interface 2770, an audio module 2780, a camera module 2791, a power management module 2795, a battery 2796, an indicator 2797, and a motor 2798.

The processor 2710 may control multiple hardware and software components connected to the processor 2710 by running, e.g., an OS or application programs, and the processor 2710 may process and compute various data. The processor 2710 may be implemented in, e.g., a system on chip (SoC). According to an embodiment of the present disclosure, the processor 2710 may further include a graphic processing unit (GPU) and/or an image signal processor. The processor 2710 may include at least some (e.g., the cellular module 2721) of the components shown in FIG. 27. The processor 2710 may load a command or data received from at least one of other components (e.g., a non-volatile memory) on a volatile memory, process the command or data, and store various data in the non-volatile memory.

The communication module 2720 may have the same or similar configuration to the communication interface 170 of FIG. 1. The communication module 2720 may include, e.g., a cellular module 2721, a Wi-Fi module 2723, a Bluetooth module 2725, a GNSS module 2727 (e.g., a GPS module, a Glonass module, a Beidou module, or a Galileo module), an NFC module 2728, and a radio frequency (RF) module 2729.

The cellular module 2721 may provide voice call, video call, text, or Internet services through, e.g., a communication network. The cellular module 2721 may perform identification or authentication on the electronic device 2701 in the communication network using the subscriber identification module 2724 (e.g., a SIM card). According to an embodiment of the present disclosure, the cellular module 2721 may perform at least some of the functions providable by the processor 2710. According to an embodiment of the present disclosure, the cellular module 2721 may include a CP.

The Wi-Fi module 2723, the Bluetooth module 2725, the GNSS module 2727, or the NFC module 2728 may include a process for, e.g., processing data communicated through the module. At least some (e.g., two or more) of the cellular module 2721, the Wi-Fi module 2723, the Bluetooth module 2725, the GNSS module 2727, or the NFC module 2728 may be included in a single integrated circuit (IC) or an IC package.

The RF module 2729 may communicate data, e.g., communication signals (e.g., RF signals). The RF module 2729 may include, e.g., a transceiver, a power amp module (PAM), a frequency filter, a low noise amplifier (LNA), or an antenna. According to an embodiment of the present disclosure, at least one of the cellular module 2721, the Wi-Fi module 2723, the Bluetooth module 2725, the GNSS module 2727, or the NFC module 2728 may communicate RF signals through a separate RF module.

The subscription identification module 2724 may include, e.g., a card including a subscriber identification module and/or an embedded SIM, and may contain unique identification information (e.g., an integrated circuit card identifier (ICCID) or subscriber information (e.g., an international mobile subscriber identity (IMSI)).

The memory 2730 (e.g., the memory 130) may include, e.g., an internal memory 2732 or an external memory 2734. The internal memory 2732 may include at least one of, e.g., a volatile memory (e.g., a dynamic RAM (DRAM), a static RANI (SRAM), a synchronous dynamic RAM (SDRAM), etc.) or a non-volatile memory (e.g., a one time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid state drive (SSD).

The external memory 2734 may include a flash drive, e.g., a compact flash (CF) memory, a secure digital (SD) memory, a micro-SD memory, a mini-SD memory, an extreme digital (xD) memory, a multi-media card (MMC), or a memory Stick™. The external memory 2734 may be functionally and/or physically connected with the electronic device 2701 via various interfaces.

The sensor module 2740 may measure a physical quantity or detect an operational state of the electronic device 2701, and the sensor module 240 may convert the measured or detected information into an electrical signal. The sensor module 2740 may include at least one of, e.g., a gesture sensor 2740A, a gyro sensor 2740B, an atmospheric pressure sensor 240C, a magnetic sensor 2740D, an acceleration sensor 2740E, a grip sensor 2740F, a proximity sensor 2740G, a color sensor 2740H (e.g., a red-green-blue (RGB) sensor, a bio sensor 2740I, a temperature/humidity sensor 2740J, an illumination sensor 2740K, or an ultra violet (UV) sensor 2740M. Additionally or alternatively, the sensing module 2740 may include, e.g., an E-nose sensor, an electromyography (EMG) sensor, an electroencephalogram (EEG) sensor, an electrocardiogram (ECG) sensor, an infrared (IR) sensor, an iris sensor, or a finger print sensor. The sensor module 2740 may further include a control circuit for controlling at least one or more of the sensors included in the sensing module. According to an embodiment of the present disclosure, the electronic device 2701 may further include a processor configured to control the sensor module 2740 as part of the processor 2710 or separately from the processor 2710, and the electronic device 2701 may control the sensor module 2740 while the processor 2710 is in a sleep mode.

The input unit 2750 may include, e.g., a touch panel 2752, a (digital) pen sensor 2754, a key 2756, or an ultrasonic input device 2758. The touch panel 2752 may use at least one of capacitive, resistive, infrared, or ultrasonic methods. The touch panel 2752 may further include a control circuit. The touch panel 2752 may further include a tactile layer and may provide a user with a tactile reaction.

The (digital) pen sensor 2754 may include, e.g., a part of a touch panel or a separate sheet for recognition. The key 2756 may include e.g., a physical button, optical key or keypad. The ultrasonic input device 2758 may sense an ultrasonic wave generated from an input tool through a microphone (e.g., the microphone 2788) to identify data corresponding to the sensed ultrasonic wave.

The display 2760 (e.g., the display 160) may include a panel 2762, a hologram device 2764, or a projector 2766. The panel 2762 may have the same or similar configuration to the display 160 of FIG. 1. The panel 2762 may be implemented to be flexible, transparent, or wearable. The panel 2762 may also be incorporated with the touch panel 2752 in a module. The hologram device 2764 may make three dimensional (3D) images (holograms) in the air by using light interference. The projector 2766 may display an image by projecting light onto a screen. The screen may be, for example, located inside or outside of the electronic device 2701. In accordance with an embodiment of the present disclosure, the display 2760 may further include a control circuit to control the panel 2762, the hologram device 2764, or the projector 2766.

The interface 2770 may include e.g., an HDMI 2772, a USB 2774, an optical interface 2776, or a D-subminiature (D-sub) 2778. The interface 2770 may be included in e.g., the communication interface 170 shown in FIG. 1. Additionally or alternatively, the interface 2770 may include a mobile high-definition link (MHL) interface, a SD card/multimedia card (MMC) interface, or infrared data association (IrDA) standard interface.

The audio module 2780 may convert a sound into an electric signal or vice versa, for example. At least a part of the audio module 2780 may be included in e.g., the input/output interface 145 as shown in FIG. 1. The audio module 2780 may process sound information input or output through e.g., a speaker 2782, a receiver 2784, an earphone 2786, or a microphone 2788.

The camera module 2791 may be a device for capturing still images and videos, and may include, according to an embodiment of the present disclosure, one or more image sensors (e.g., front and back sensors), a lens, an image signal processor (ISP), or a flash such as an LED or xenon lamp.

The power manager module 2795 may manage power of the electronic device 2701, for example. Although not shown, according to an embodiment of the present disclosure, the power manager module 2795 may include a power management integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 2796, a voltage, a current, or a temperature while the battery 2796 is being charged. The battery 2796 may include, e.g., a rechargeable battery or a solar battery.

The indicator 2797 may indicate a particular state of the electronic device 2701 or a part (e.g., the processor 2710) of the electronic device, including e.g., a booting state, a message state, or recharging state. The motor 2798 may convert an electric signal to a mechanical vibration and may generate a vibrational or haptic effect. Although not shown, a processing unit for supporting mobile TV, such as a GPU may be included in the electronic device 2701. The processing unit for supporting mobile TV may process media data conforming to a standard for digital multimedia broadcasting (DMB), digital video broadcasting (DVB), or mediaFlo™.

Each of the aforementioned components of the electronic device may include one or more parts, and a name of the part may vary with a type of the electronic device. The electronic device in accordance with various embodiments of the present disclosure may include at least one of the aforementioned components, omit some of them, or include other additional component(s). Some of the components may be combined into an entity, but the entity may perform the same functions as the components may do.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of application specific integrated circuit (ASIC) chips, field programmable gate arrays (FPGAs), or programmable logic arrays (PLAs) that perform some operations, which have already been known or will be developed in the future.

According to an embodiment of the present disclosure, at least a part of the device (e.g., modules or their functions) or method (e.g., operations) may be implemented as instructions stored in a computer-readable storage medium e.g., in the form of a program module. The instructions, when executed by a processor (e.g., the processor 120), may enable the processor to carry out a corresponding function. The computer-readable storage medium may be e.g., the memory 130.

The computer-readable storage medium may include a hardware device, such as hard discs, floppy discs, and magnetic tapes (e.g., a magnetic tape), optical media such as compact disc ROMs (CD-ROMs) and DVDs, magneto-optical media such as floptical disks, ROMs, RAMs, Flash Memories, and/or the like. Examples of the program instructions may include not only machine language codes but also high-level language codes which are executable by various computing means using an interpreter. The aforementioned hardware devices may be configured to operate as one or more software modules to carry out various embodiments of the present disclosure, and vice versa.

Modules or programming modules in accordance with various embodiments of the present disclosure may include at least one or more of the aforementioned components, omit some of them, or further include other additional components. Operations performed by modules, programming modules or other components in accordance with various embodiments of the present disclosure may be carried out sequentially, simultaneously, repeatedly, or heuristically.

Furthermore, some of the operations may be performed in a different order, or omitted, or include other additional operation(s).

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A wearable electronic device, the wearable electronic device comprising:
   a housing;
   a touch screen display disposed on a first side of the housing;
   a first coil disposed on a second side of the housing opposite to the first side;
   a second coil disposed under the touch screen display; and
   at least one processor configured to:
      detect, using the first coil, a contact of a first body portion,
      in response to detecting the contact of the first body portion, generate a first current through the first coil by applying power to the first coil,
      detect a second current induced across the second coil after a current is induced across the first body portion based on the generated first current, and
      obtain user body information based on the detected second current,
   wherein the user body information includes at least one of body composition information, body fat information, body fat-free information, body water information, body muscle information, body protein information, or body mineral information.

2. The wearable electronic device of claim 1,
   wherein the second current is induced across the second coil according to a contact of a second body portion on the touch screen display.

3. The wearable electronic device of claim 2,
   wherein the second current is induced across the second coil based on a magnetic field generated by a current induced across the second body portion.

4. The wearable electronic device of claim 1, wherein the at least one processor is further configured to:
   detect, using the second coil, a touch input on the touch screen display.

5. The wearable electronic device of claim 1, wherein the second coil is formed of a transparent film and embedded in the wearable electronic device.

6. The wearable electronic device of claim 1, further comprising:
   a shielding sheet disposed between the first coil and the second coil,
   wherein the shielding sheet is configured to prevent a magnetic field generated between the first coil and the second coil.

7. The wearable electronic device of claim 1, wherein the at least one processor is further configured to:
   charge the wearable electronic device using a third current induced across the second coil by a magnetic field generated from outside the wearable electronic device.

8. The wearable electronic device of claim 1, wherein the at least one processor is further configured to:
   identify a difference between the generated first current and the detected second current, and
   obtain the user body information based on the difference between the generated first current and the detected second current.

9. The wearable electronic device of claim 1, wherein the at least one processor is further configured to:
   detect a first voltage at the first coil and a second voltage at a position of a contact of a second body portion on the touch screen display, and
   obtain the user body information based on the detected first voltage and the detected second voltage.

10. The wearable electronic device of claim 9,
    wherein the at least one processor is further configured to:
       identify a preset threshold voltage, and
       obtain the user body information based on the identified preset threshold voltage, the detected first voltage, and the detected second voltage, and
    wherein the preset threshold voltage is set to a voltage sensed by the contact of the second body portion on the touch screen display.

11. The wearable electronic device of claim 1, wherein the at least one processor is further configured to:
    identify an area of a contact of a second body portion on the touch screen display, and
    compensate for the obtained user body information based on the identified area of the contact of the second body portion.

12. A method for controlling a wearable electronic device comprising a housing, a touch screen display disposed on a first side of the housing, a first coil disposed on a second side of the housing opposite to the first side, a second coil disposed under the touch screen display, and at least one processor, the method comprising:
    detecting, by the at least one processor, using the first coil, a contact of a first body portion;
    in response to detecting the contact of the first body portion, generating, by the at least one processor, a first current through the first coil by applying power to the first coil;
    detecting, by the at least one processor, a second current induced across the second coil after a current is induced across the first body portion based on the generated first current; and
    obtaining, by the at least one processor, user body information based on the detected second current,
    wherein the user body information includes at least one of body composition information, body fat information, body fat-free information, body water information, body muscle information, body protein information, or body mineral information.

13. The method of claim 12, wherein the second current is induced across the second coil according to a contact of a second body portion on the touch screen display.

14. The method of claim 13, wherein the second current is induced across the second coil based on a magnetic field generated by a current induced across the second body portion.

15. The method of claim 12, further comprising:
    detecting, by the at least one processor, using the second coil, a touch input on the touch screen display.

16. The method of claim 12, further comprising:
    charging, by the at least one processor, the wearable electronic device using a third current induced across the second coil by a magnetic field generated from outside the wearable electronic device.

17. The method of claim 12, wherein the obtaining of the user body information based on the detected second current comprises:

identifying, by the at least one processor, a difference between the generated first current and the detected second current; and obtaining, by the at least one processor, the user body information based on the difference between the generated first current and the detected second current.

18. The method of claim 12, further comprising:

detecting, by the at least one processor, a first voltage at the first coil and a second voltage at a position of a contact of a second body portion on the touch screen display; and obtaining, by the at least one processor, the user body information based on the detected first voltage and the detected second voltage.

19. The method of claim 18, wherein the obtaining of the user body information based on the detected first voltage and the detected second voltage comprises:

identifying, by the at least one processor, a preset threshold voltage, and obtaining, by the at least one processor, the user body information based on the identified preset threshold voltage, the detected first voltage, and the detected second voltage, and wherein the preset threshold voltage is set to a voltage sensed by the contact of the second body portion on the touch screen display.

20. The method of claim 12, further comprising:

identifying, by the at least one processor, an area of a contact of a second body portion on the touch screen display; and compensating, by the at least one processor, for the obtained user body information based on the identified area of the contact of the second body portion.

* * * * *